United States Patent [19]

Suzuki et al.

[11] Patent Number: 4,920,969

[45] Date of Patent: May 1, 1990

[54] AMBULATORY PHYSIOLOGICAL EVALUATION SYSTEM INCLUDING CARDIAC MONITORING

[75] Inventors: Arata Suzuki, Ramsey, N.J.; William T. Tyberg, Springvalley, N.Y.; George Banks, Emerson, N.J.; Marcia Suzuki, Ramsey, N.J.

[73] Assignee: Capintec, Inc., Ramsey, N.J.

[21] Appl. No.: 46,854

[22] Filed: May 7, 1987

Related U.S. Application Data

[62] Division of Ser. No. 785,549, Oct. 8, 1985, abandoned.

[51] Int. Cl.$^5$ .............................................. A61B 5/04
[52] U.S. Cl. ................................................... 128/659
[58] Field of Search ............... 128/644, 659, 641, 721, 128/733, 736

[56] References Cited

U.S. PATENT DOCUMENTS

| | | | |
|---|---|---|---|
| 3,409,007 | 11/1968 | Fuller | 128/644 |
| 3,534,727 | 10/1970 | Roman | 128/644 |
| 3,580,243 | 5/1971 | Johnson | 128/696 |
| 3,824,299 | 7/1974 | Brown et al. | 164/41 |
| 3,840,890 | 10/1974 | Sunderland | 360/32 |
| 4,015,592 | 4/1977 | Bradley-Moore | 128/654 |
| 4,192,318 | 3/1980 | Dam et al. | 128/708 |
| 4,197,836 | 4/1980 | Wagner et al. | 128/654 |
| 4,217,642 | 8/1980 | Dam et al. | 364/413.07 |
| 4,245,646 | 1/1981 | Ionnou et al. | 128/653 |
| 4,245,647 | 1/1981 | Randall | 128/659 |
| 4,294,259 | 10/1981 | Picunko et al. | 128/653 |
| 4,333,475 | 6/1982 | Moreno et al. | 128/711 |
| 4,393,371 | 7/1983 | Morgan-Smith | 341/123 |
| 4,404,973 | 9/1983 | Lancaster et al. | 128/654 |
| 4,572,197 | 2/1986 | Moore et al. | 128/644 |

OTHER PUBLICATIONS

"Ambulatory Holter Electrocardiography: Choice of Technologies and Clinical Uses", J. Morganroth, Annals of Internal Medicine, vol. 102, No. 1, pp. 73–81, Jan. 1985.

"Beat-to-Beat Left Ventricular Performance Assessed From the Equilibrium Cardiac Blood Pool Using a Computerized Nuclear Probe", H. J. Berger et al., Circulation, vol. 63, No. 1, pp. 133–141, Jan. 1981.

The Vest, Moore et al., Reprinted from Emission Computer Tomography 1983, Society of Nuclear Medicine, 475 Park Avenue South, New York, N.Y. 10016, pp. 264–275.

An Ambulatory Ventricular Function Monitor: Valida- (List continued on next page.)

Primary Examiner—Francis Jaworski
Attorney, Agent, or Firm—Fleit, Jacobson, Cohn, Price, Holman & Stern

[57] ABSTRACT

An ambulatory physiological evaluation system including a main and a background gamma radiation detector provided in a vestlike garment worn by a patient for the purpose of monitoring and/or diagnosing the patient's physiological activities during a prescribed period of time. Also included is an apparatus and method for determining the exact location of the left ventricle of the heart, positioning the main radiation detector relative to the left ventricle, and maintaining the position of the main radiation detector relative to the left ventricle during an ambulatory study period. The ambulatory physiological evaluation system also contains electronic circuitry which monitors and processes information obtained from the radiation detectors. Information from the main and auxiliary detectors, as well as ECG electrodes is recorded on a portable cassette recorder. After the information has been recorded over a desired period of time, the information is presented, through an interface and an analog to digital converter, to the memory of a stand alone computer located in a hospital or office. The computer calculates such items as R-R time intervals, electrocardiagram and time-activity curves, and displays these items and other physiological data for both the main and auxiliary detectors. From the calculations made by the computer, average heart rate, number of aberrant beats, left ventricular ejection fraction and relative cardiac blood volume and other values of physiological significance may be calculated for a time interval of interest.

6 Claims, 12 Drawing Sheets

OTHER PUBLICATIONS tion and Preliminary Clinical Results, Wison et al., Reprinted from the Sep. 1 issue of The American Journal of Cardiology, A Yorke Medical Journal, Published by Technical Publishing, pp. 601–606.

Wilson et al., An Ambulatory Ventricular Function Monitor: Validation and Preliminary Results, The American Journal of Cardiology, vol. 53, Sep. 1983, pp. 601–606.

Moore et al., The Vest-Description of the Instrument and Initial Validation: A Device for the Ambulatory Measurement of Ejection Fraction, Emission Computed Tomography, Society of Nuclear Medicine, 1983, pp. 263–274.

Wagner, The Nuclear Cardiac Probe, Hospital Practice, Apr. 1982, vol. 17, No. 4, pp. 163–177.

Ambulatory Monitoring of LV Function, Cardio, Oct. 1984, p. 21.

Osbakken et al., The Normal Adult Gated Blood Pool Scan: A Qualitative Analysis, Radio Graphics, vol. 4, No. 2, Mar. 1984, pp. 315–326.

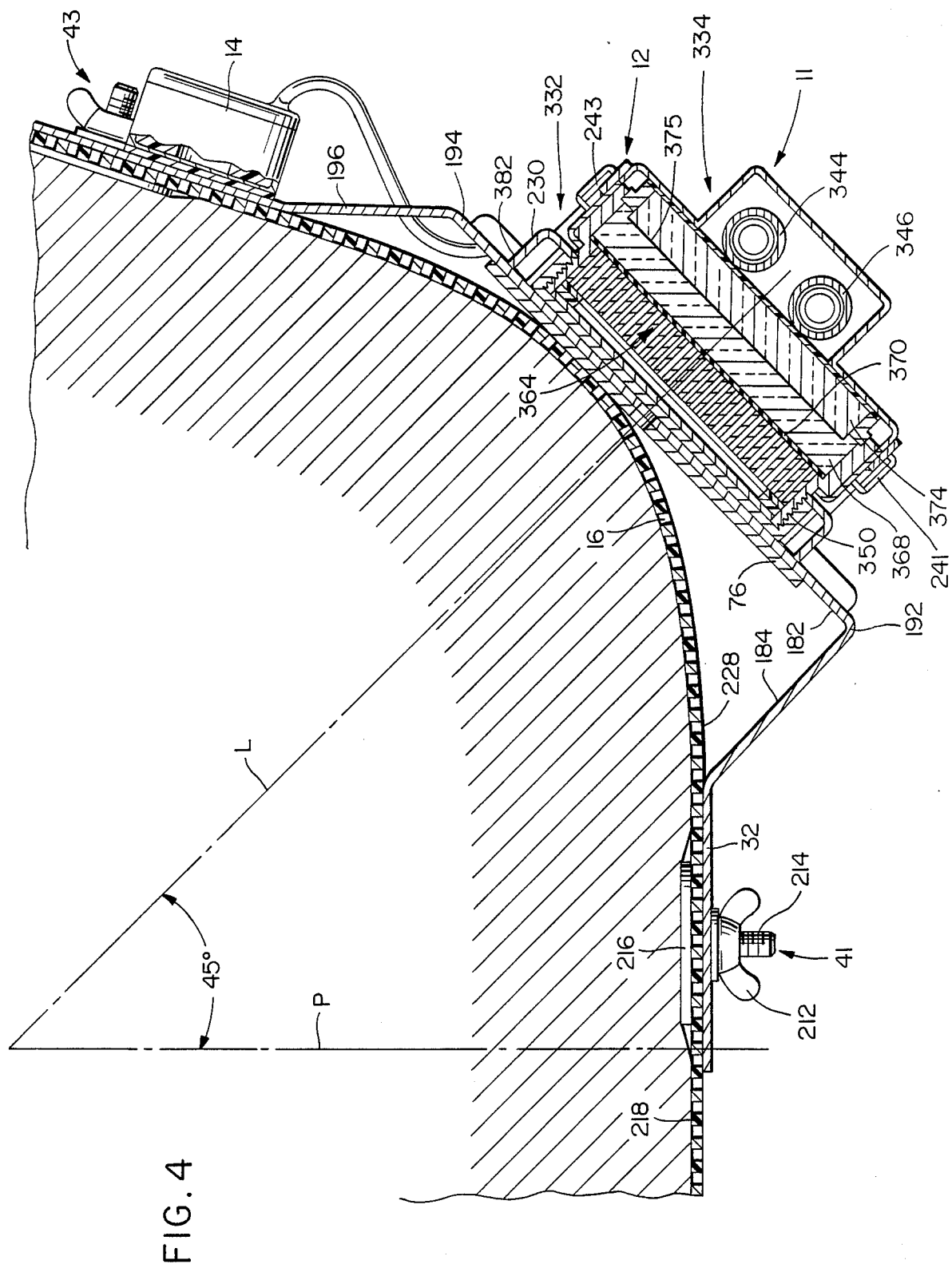

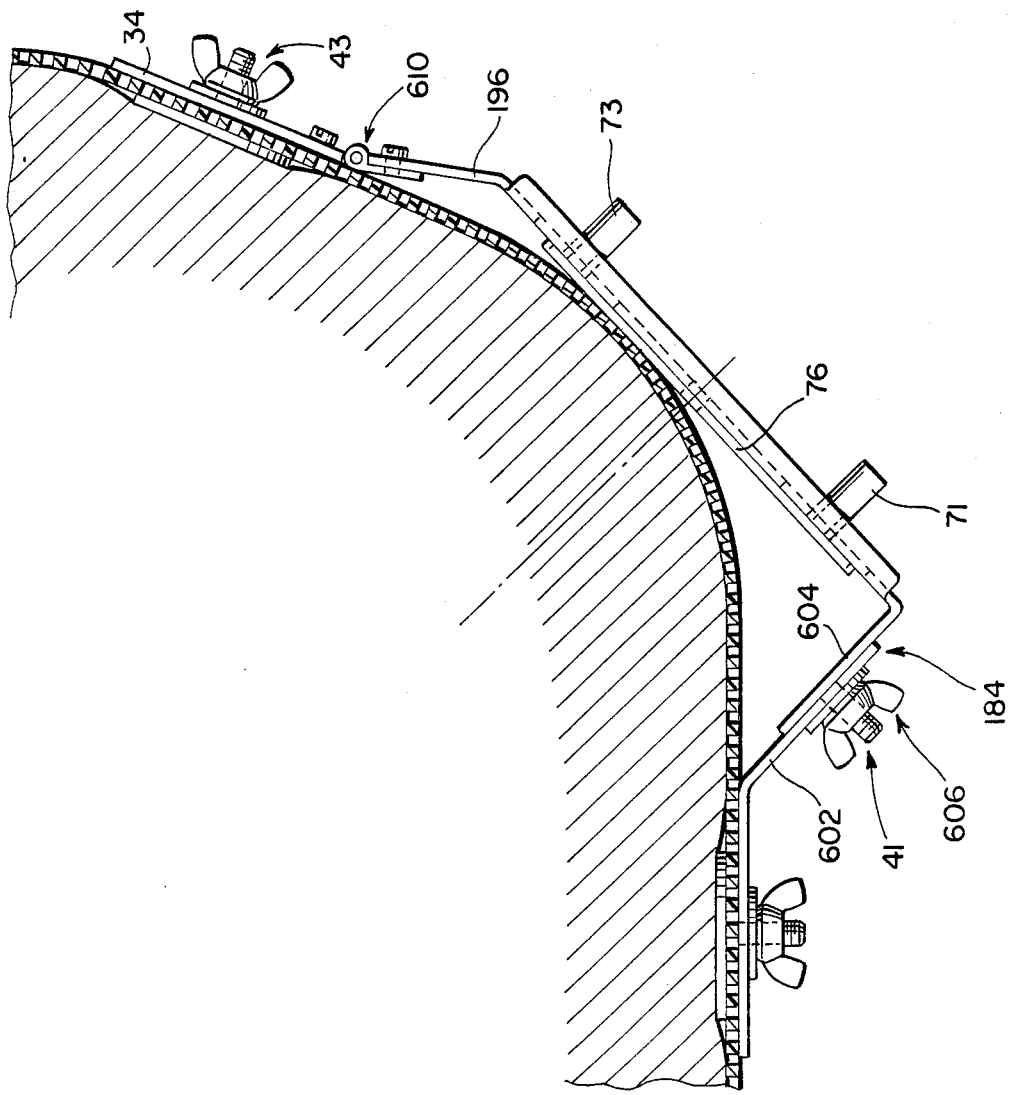
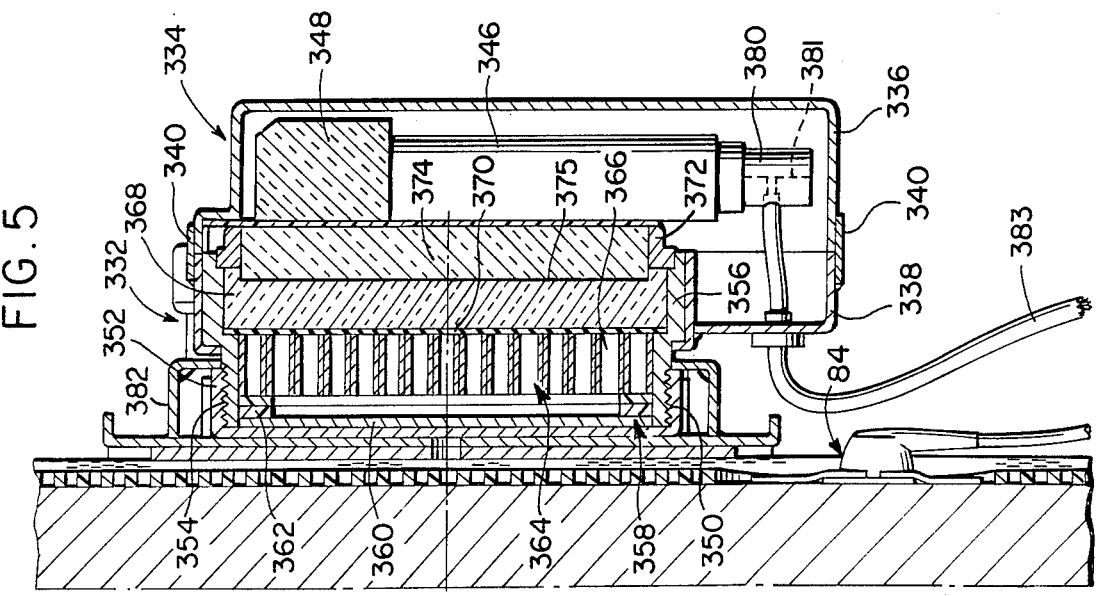

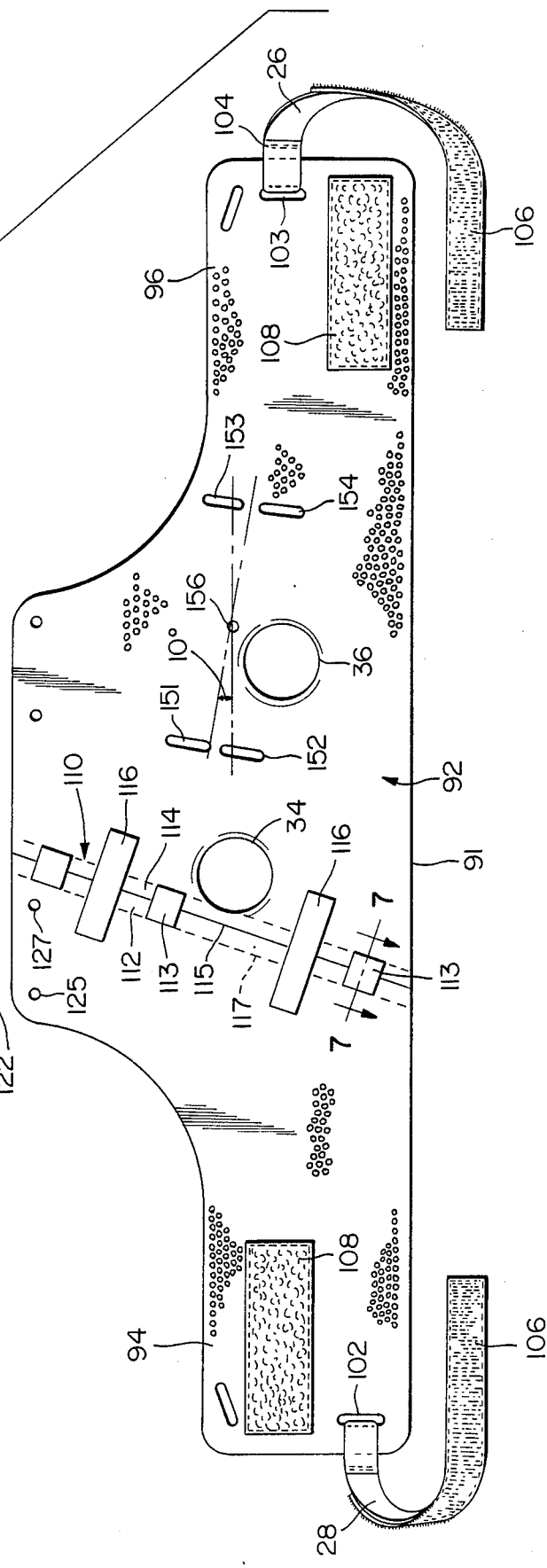
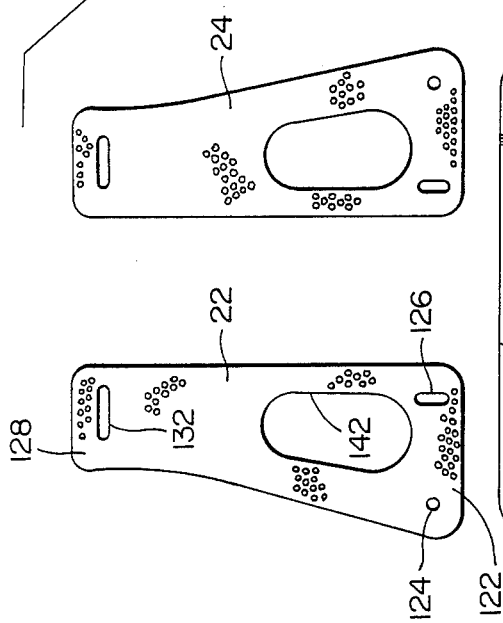
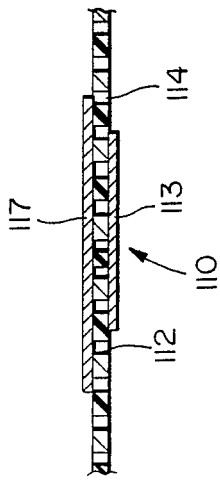
FIG. 6
FIG. 7

CARRIER FREQ =
$f_0$ = n SAMPLES/SECONDS

16ms

AMBULATORY PHYSIOLOGICAL EVALUATION SYSTEM INCLUDING CARDIAC MONITORING

This is a divisional of application Ser. No. 785,549, filed Oct. 8, 1985, and now abandoned.

FIELD OF THE INVENTION

The present invention relates to measurement of physiological parameters through use of radionuclide detectors, in general, and to an evaluation system employing nuclear medicine to monitor and diagnosis a patient's physiological activities with the radionuclide detectors and miniature electronics being incorporated into a vestlike garment worn outside the chest of the patient.

BACKGROUND OF THE INVENTION

From statistics taken from the American Heart Association, it is known that over 40 million Americans have some form of heart and/or blood vessel disease. Over one million deaths occur annually due to cardiovascular disease, and over 600,000 deaths are the result of coronary artery disease. Accurate diagnosis and appropriate therapy are critical to the management of a patient with cardiovascular disease.

Many diagnostic tools are available to diagnose coronary artery disease or heart attack. These include blood tests, electrocardiograms (resting or during stress), angiography (conventional and digital subtraction techniques), ultrasound and nuclear cardiology techniques. The nuclear cardiology techniques, which employ nuclear imaging, are the only techniques capable of functional assessment of the heart. Nuclear cardiology techniques are capable of detecting infractions, ischemia, coronary artery disease, assessment of birth defects and predicting effectiveness of cardiac medications and/or surgical intervention.

Relative to other diagnostic imaging techniques, nuclear imaging has several important advantages which account for its current growth. Most important, nuclear imaging can provide diagnostic information related to cardiac function rather than just anatomy. By utilizing radioactive tracers, nuclear imaging of left ventricular function (LVF) can monitor physiological processes over time, whereas most other imaging methods can produce only a static picture. Therefore, the use of radionuclides in diagnosis of cardiovascular disease is continually expanding.

In addition to the diagnostic imaging procedure, an important need exists for a device which permits nuclear and ECG measurements to be made in an ambulatory mode. This need exists because, during the performance of ordinary activities associated with daily living, left ventricular function varies over a wide range in both the healthy and diseased heart. These changes in left ventricular function, brought about by such ordinary activities as walking, climbing stairs, psychological stress, exposure to severe temperature changes, etc., may equal or exceed those observed in a laboratory during the performance of a nuclear cardiac dynamic function study. In coronary artery disease, the accurate and continuous measurement of changes in cardiac physiology such as ischemia, arrhythmia, fall in ejection fraction, or a rise in relative cardiac blood volume can assist in the management of the patient's disease. In addition, measurements made before and after surgery or drug therapy may offer additional insights into the impact of these treatments on left ventricular function or dysfunction.

Likewise, in silent ischemia (also defined by many cardiologists as left ventricular dysfunction), where electrocardiographic changes may possibly be observed after several minutes of ECG recording, left ventricular function changes may be observed in a matter of seconds after the onset of the decompensation. The effective monitoring of these left ventricular changes (such as, increase in end systolic volume) result in better design and administration of a proper therapy regime.

An example of a nuclear cardiac probe designed to meet the need for noninvasive evaluation of rapidly developing flanges in global left ventricular function is discussed in "The Nuclear Cardiac Probe," by Dr. Henry N. Wagner Jr., *Hospital Practice*, April, 1982, Volume 17, Number 4, pages 163-177. The probe discussed in the article is housed in a console which may be moved by casters from place to place. The probe, however, does not offer a system that can be easily carried by the patient.

Ambulatory monitoring of left ventricular function has been shown to be possible with the development of a miniaturized system of radionuclide detectors and electronics incorporated into a vestlike garment and worn outside the chest. See, for example, "An Ambulatory Ventricular Function Monitor: Validation and Preliminary Clinical Results," by Drs. Wilson, Sullivan, Moore, Zielonka, Alpert, Boucher, McKusick and Strauss, *The American Journal of Cardiology*, Sept. 1, 1983, Volume 52, pages 601-606.

A truly ambulatory cardiac evaluation system has several potential areas of application. Firstly, it may be particularly useful in evaluating the incidence of silent ischemia. There is now tremendous interest in the cardiology community in the idea that many of the episodes of myocardial ischemia in patients with coronary disease are probably pain free. There has been much talk that ST segment changes seen on Holter recordings may represent ischemia. That, however, has been extremely controversial because people are aware of other circumstances where ST segment changes are not caused by ischemia. Therefore, the issue has been to identify changes in ventricular function which could be caused by ischemia in association with the ST changes. This has been something which is very difficult to identify in ambulatory subjects. The present invention can make these measurements at the same time.

The second application is to define the impact of drug therapy. This is particularly important in patients who have just been diagnosed as having coronary disease, hypertension or some other circumstances where there is a need to know whether the drug therapy has depressed the patients ventricular function. The patient can be studied before and after taking the drug. In both cases, the patient pursues his/her daily activities to see whether the drug has negatively impacted cardiac function. Currently this is done by merely monitoring the patients reaction—do they feel tired, get out of breath, etc The third area is to define the appropriate exercise prescription in both people who do not have known heart disease, but are just out of shape, and in people who have known heart disease. It is particularly useful on patients after thee have had a myocardial infarction where the patient should begin exercising on a gradual basis so that they do not exercise to a point where their ventricular function diminishes.

Thus, there is still a need for an ambulatory evaluation system which can be worn in relative comfort by a patient for monitoring coronary artery disease, in surgical and post operative workups, for anesthesia rehabilitation, for monitoring exercise regime, for drug and diet studies, and for monitoring the effectiveness of drug administered in the therapeutic program. The present invention is directed toward filling that need.

SUMMARY OF THE INVENTION

The present invention relates generally to an ambulatory physiological evaluatIon system including gamma radiation detectors, as cardiac monitors, utilized in the nuclear medicine field for the purpose of monitoring and/or diagnosing a patient's physiological activities, such as left ventricular function, during a prescribed period of time. In a preferred embodiment of the invention, a compact cardiac monitor having a main detector is placed generally over the heart of a patient and a radiation detector, mounted within the monitor, senses the ebb and flow of the blood through the heart by detection of the gamma rays emitted by TC-99m labeled blood cells. In order to accurately measure blood volume, the radiation detector must be precisely positioned relative to the heart and this relationship must be maintained during the entire detecting period. The present invention provides an apparatus and method for determining the exact location of the left ventricle of the patient's heart, positioning the cardiac monitor relative to the left ventricle, and maintaining the position of the cardiac monitor relative to the left ventricle during an ambulatory study period.

The starting point for the inventive ambulatory physiological evaluation system is a vest made of a flexible plastic material, such as "Aquaplast", which contains a pattern of ventilation holes. The vest is adapted to be worn on the torso of a human and contains an arrangement of shoulder straps and belts to provide for a snug, yet relatively comfortable fit. The vest is worn to provide a base to which a cardiac monitor including a main detecting device is attached and held in a precise relationship between the main detecting device and an anatomical body, such as the left ventricle of the heart.

Attachment of the cardiac monitor to the vest is accomplished through the use of a detector mounting bracket which is a lightweight, formed, metallic structure with means for attaching to both the vest and to the detecting device. The mounting bracket fastens two detecting devices, a main detector and a auxiliary detector, to the vest and provides two means for adjusting the main detector relative to the left ventricle of the heart of the wearer. First, the mounting bracket has flanges so that the bracket can be adjusted relative to the vest through fasteners movably positioned within the vest. Second, for more precise adjustment, the main detector can be adjusted plus or minus one centimeter in two directions relative to the detector mounting bracket, thereby, providing for precise adjustment of the main detector relative to the left ventricle of the heart of the wearer. A scale is provided between the main detector flange and the detector mounting bracket, reading in 5 millimeter increments. The scale precisely indicates the relative position between the mounting bracket and the main detector.

In order to properly align the detector mounting bracket relative to the left ventricle of the heart, an alignment fixture is used prior to mounting the main detector to the mounting bracket. The detector alignment fixture basically comprises a planar leveling elate to which is fastened a plate within which is embedded a centerline cursor made from lead elements. The detector alignment fixture is mounted to the face of the detector mounting bracket with four cap screws. A center guide pin on the alignment fixture enters a center hole of the detector mounting bracket and, in addition, the four posts on a floating base plate positioned behind the face of the mounting bracket, enter the four holes in the alignment fixture. The mounting bracket also has a pair of opposed flanges which aid in mounting the centerline plate. After mounting, the detector alignment fixture is centered on the detector mounting plate.

A conventional scintillation or gamma camera is brought up to the alignment fixture and adjusted for parallelism. The picture derived from the camera on a cathode ray tube (CRT) display shows the position of the cursor relative to the left ventricle of the heart. If the centerline of the cursor is within 10 millimeters of the desired position, any further adjustment can be made when the alignment fixture is removed and the main detector assembled to the mounting bracket. If the location of the centerline is further away from the left ventricle of the heart than 10 millimeters, the mount must be readjusted relative to the vest and the above procedure repeated.

The ambulatory physiological evaluation system also contains electronic circuitry which monitors and processes information obtained from the main and auxiliary detectors. A preferred embodiment of the evaluation system basically comprises a Cadmium Telluride (CdTe) detector which is used as the auxiliary detector that is responsive to the presence of a suitable radiopharmaceutical, such as TC-99m tagged red blood cells, injected into the circulatory system to provide an output signal representative of left lung activity. The CdTe detector may be placed at other locations on the body of the patient to evaluate other physiological parameters such as pulmonary, cereberal and muscular function. The cardiac monitor that includes the main detector is also responsive to the presence of a suitable radiopharmaceutical injected into the circulatory system to produce a signal which is proportional over the cardiac cycle. The signal produced by the main detector is representative of the left ventricular time activify of the heart. Both of these signals are fed in analog pulse form to a data logger which is housed in a bag worn by the patient. The data logger includes the circuitry necessary to accumulate and manipulate the data and transfer it to a portable cassette recording device also housed in the bag. Also, feeding information into the recording device are conventional ECG electrodes. After the information has been recorded over a desired period of time, the recorded information on cassette is presented, through an impedance matching interface and an analog to digital converter, to the memory of a stand alone computer located in a hospital or office. The computer calculates such items as R-R time interval, electrocardiagram and time-activity curves, and displays these items for both the main and auxiliary detectors. From the calculations made by the computer, average heart rate, number of aberrant beats, left ventricular ejection fraction and relative cardiac blood volume may be calculated for a time interval of interest.

Thus, it is the primary object of the present invention to provide truly ambulatory physiological evaluation system including cardiac monitoring.

It is another object of the present invention to provide a mounting apparatus for mounting a radiation detector in a precise relationship to an interior organ of the body of a patient.

It is a further object of the present invention to provide an apparatus to facilitate mounting of a radiation detector to an ambulatory vest in a precise relationship with the left ventricle of the heart of the wearer of the vest.

It is still an object of the present invention to provide a device for accurately recording information detected by a radiation detector that is monitoring physiological activity of a patient.

It is yet an object of the present invention to provide an information processing system for manipulating and displaying prerecorded information detected by a detector that is monitoring physiological activity of a patient.

Other objects, advantages, and features will become apparent by reference to the following detailed description and drawings.

BRIEF DESCRIPTION OF THE DRAWINGS

FIG. 4 is a top view partially in section of the evaluation system of FIG. 1.

FIG. 5 is a view taken along line 5—5 of FIG. 3.

FIG. 6 is a plan view of the basic elements constituting the vest of the evaluation system of FIG. 1.

FIG. 7 is a view taken along lines 7—7 of FIG. 6.

FIG. 8 is a view similar to FIG. 4 with the cardiac monitor removed and an alternative embodiment for the detector mounting bracket.

DETAILED DESCRIPTION OF THE PREFERRED EMBODIMENTS OVERVIEW OF EVALUATION SYSTEM

Figure 1:
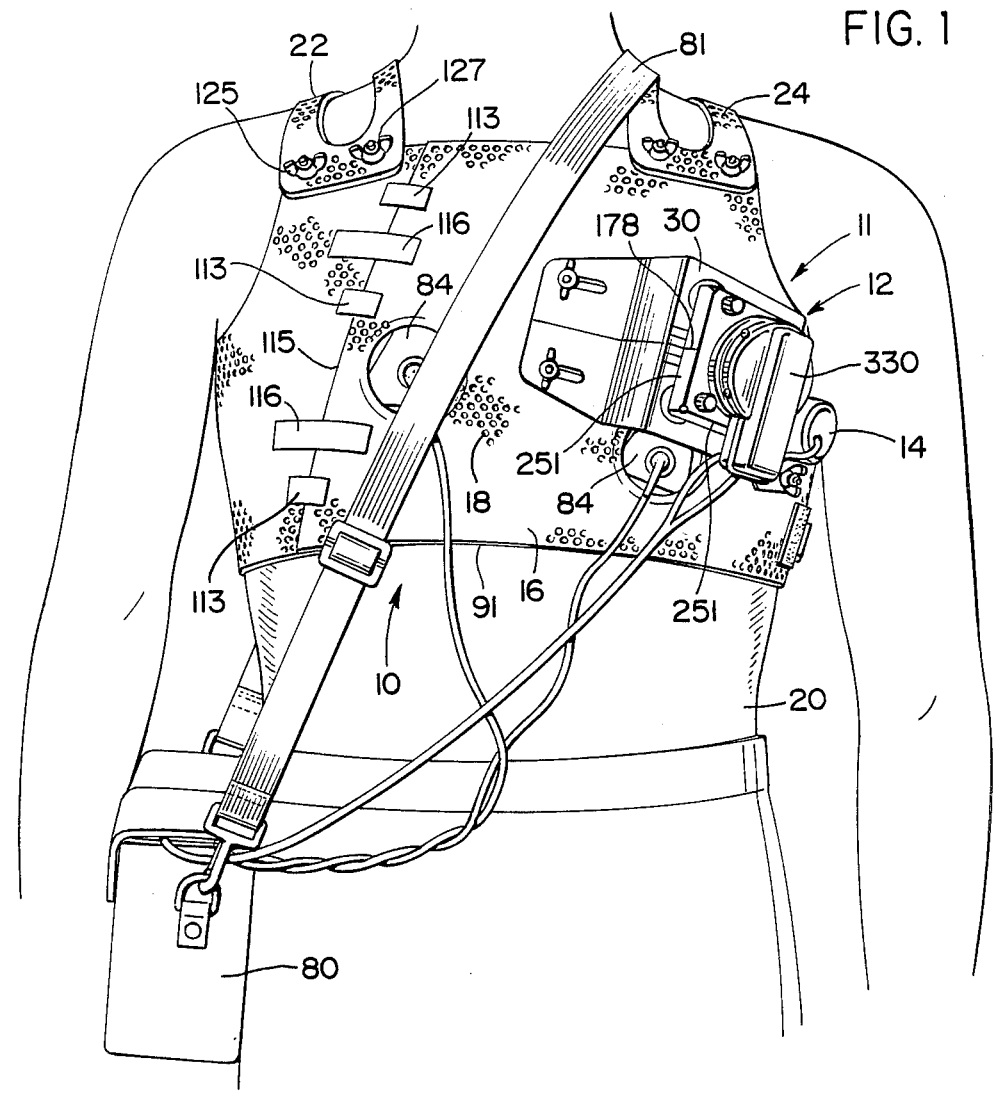
FIG. 1 is a front perspective view of a person operatively wearing an embodiment of the inventive ambulatory physiological evaluation system.

With reference to FIGS. 1-6, the present invention relates to an ambulatory physiological evaluation system, generally designated 10, including gamma radiation detectors 12 and 14 utilized in the nuclear medicine field for the purpose of monitoring and/or diagnosing a patient's physiological activities during a prescribed period of time. In a preferred embodiment of the invention, a compact cardiac monitor 11 including a main detector 12 is placed generally over the heart of a patient and a radiation detector, mounted within the monitor, senses the ebb and flow of the blood through the heart by detection of the gamma rays emitted by TC-99m labeled blood cells. In order to accurately measure blood volume, the radiation detector must be precisely positioned relative to the heart and this relationship must be maintained during the entire detecting period. The present invention provides an apparatus and method for determining the exact location of the left ventricle, positioning the cardiac monitor relative to the left ventricle, and maintaining the position of the cardiac monitor relative to the left ventricle during an ambulatory study period.

With reference to FIGS. 1 through 7, the starting point for the inventive ambulatory physiological evaluation system is a vest 16 made of a flexible plastic material, such as Aquaplast, which contains a pattern of ventilation holes 18. The vest is adapted to be worn on the torso 20 of a human and contains an arrangement of shoulder straps or shoulder supports 22,24 and belts 26,28 to provide for a snug, yet comfortable fit.

The vest is worn to provide a base to which a detecting assembly in the form of a cardiac monitor 11 is attached and held in a precise relationship between the detecting device and an anatomical body, such as the left ventricle of the heart.

Attachment of the detecting device to the vest is accomplished through the use of a detector mounting bracket 30 which is a lightweight, formed structure with means for attaching to both the vest and to the detecting device. In a preferred embodiment, the mounting bracket is made from aluminum, but could be made from plastic or other suitable material. The mounting bracket fastens two detecting devices, the main detector 12 and the auxiliary detector 14, to the vest and provides two means for adjusting the main detector relative to the left ventricle of the heart of the wearer. First, the mounting bracket has flanges 32 and 34 so that the bracket can be adjusted relative to the vest through four fasteners 41-44 movably positioned within the vest. Second, for more precise adjustment, the main detector 12 can be adjusted plus or minus one centimeter in two directions relative to the detector mounting bracket, thereby, providing for a precise adjustment of the main detector relative to the left ventricle of the heart of the wearer. A scale 36 is provided between the main detector flange and the detector mounting bracket, reading in 5 millimeter increments.

The scale precisely indicates the relative position between the mounting bracket and the main detector.

In order to properly align the detector mounting bracket relative to the left ventricle of the heart, an alignment fixture 50 is used prior to mounting the main detector to the mounting bracket. The detector alignment fixture basically comprises an elongated, planar leveling plate 52 to which is fastened a centering plate 54 within which is embedded a centerline cursor made from lead elements 58. The detector alignment fixture is mounted to the face of the detector mounting bracket with four fasteners, such as cap screws. A center guide pin 60 on the alignment fixture enters a center hole 62 of the detector mounting bracket and in addition the four posts 71-74 on a floating base plate 76 positioned behind the face of the mounting bracket, must enter the four holes in the alignment fixture 54. The mounting bracket also has a pair of opposed, upwardly extending flanges 201 and 203, which aid in aligning and mounting the centering plate. After mounting, the detector alignment fixture is centered and made parallel with the face 162 of on the detector mounting plate 30.

A conventional scintillation or gamma camera (not shown) is brought up to the alignment fixture and adjusted for parallelism. The reason the gamma camera must be adjusted so that its focal plane is parallel to the face of the alignment fixture is because the holes of the collimator found in the main detector each have a narrow field of view. The picture derived from the gamma camera on a cathode ray tube (CRT) display (not shown) shows the position of the cursor 56 relative to the left ventricle of the heart. If the centerline of the cursor is within 10 millimeters of the desire position, any further adjustment can be made when the alignment fixture is removed and the main detector 12 assembled to the mounting bracket. If the location of the centerline is further away from the left ventricle of the heart than 10 millimeters, the mount must be readjusted relative to the vest and the above procedure repeated.

Figure 17:
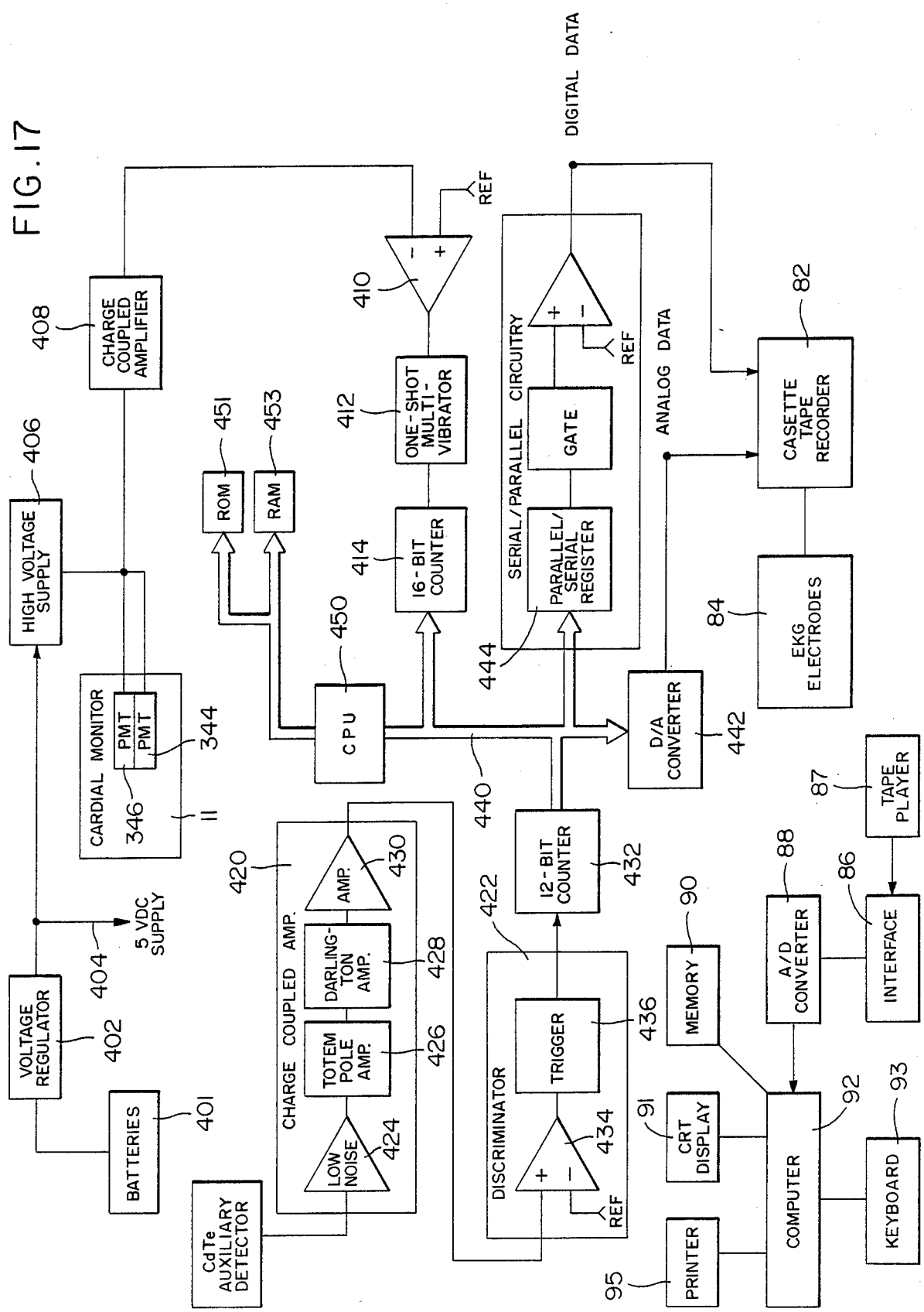
FIG. 17 is a block diagram of the electronic portion of the evaluation system of FIG. 1.

As shown in FIGS. 17 and 18, the ambulatory physiological evaluation system 10 also contains electronic circuitry which monitors and processes information obtained from the main and auxiliary detectors. A preferred embodiment of the evaluation system basically comprises a Cadmium Telluride (CdTe) detector 14 which is used as the auxiliary detector that is responsive to the presence of a suitable radio pharmaceutical TC-99m tagged red blood cells, injected into the circulatory system to provide an output signal representative of left lung or background activity. A cardiac monitor 11 includes the main detector 12 which is also responsive to the presence of a suitable radiopharmaceutical injected into the circulatory system to produce a signal which is proportional over the cardiac cycle. The signal produced by the main detector is representative of the left ventricular time activity of the heart. Both of these signals are fed in analog pulse form to a data logger which is housed in a bag 80 worn by the patient by way of shoulder strap 81. The data logger includes the circuitry necessary to accumulate and manipulate the data and transfer it to a portable cassette recording device 82, also housed in the bag. Also, feeding information into the recording device are conventional ECG electrodes 84. After the information has been recorded over a desired period of time, the recorded information is presented, through a tape player 87 an impedance matching interface 86 and an analog to digital converter 88, to the memory 90 of a stand alone computer 92 located in a hospital or office. The computer calculates and analyzes such items as R-R time interval, electrocardiagram: and time-activity curves, and/or displays these items in eye readable form for both the main and auxiliary detectors From the calculations made by the computer, such items as average heart rate, number of aberrant beats, left ventricular ejection fraction and relative cardiac blood volume may be calculated for a time interval of interest.

Ambulatory Vest

Figure 2:
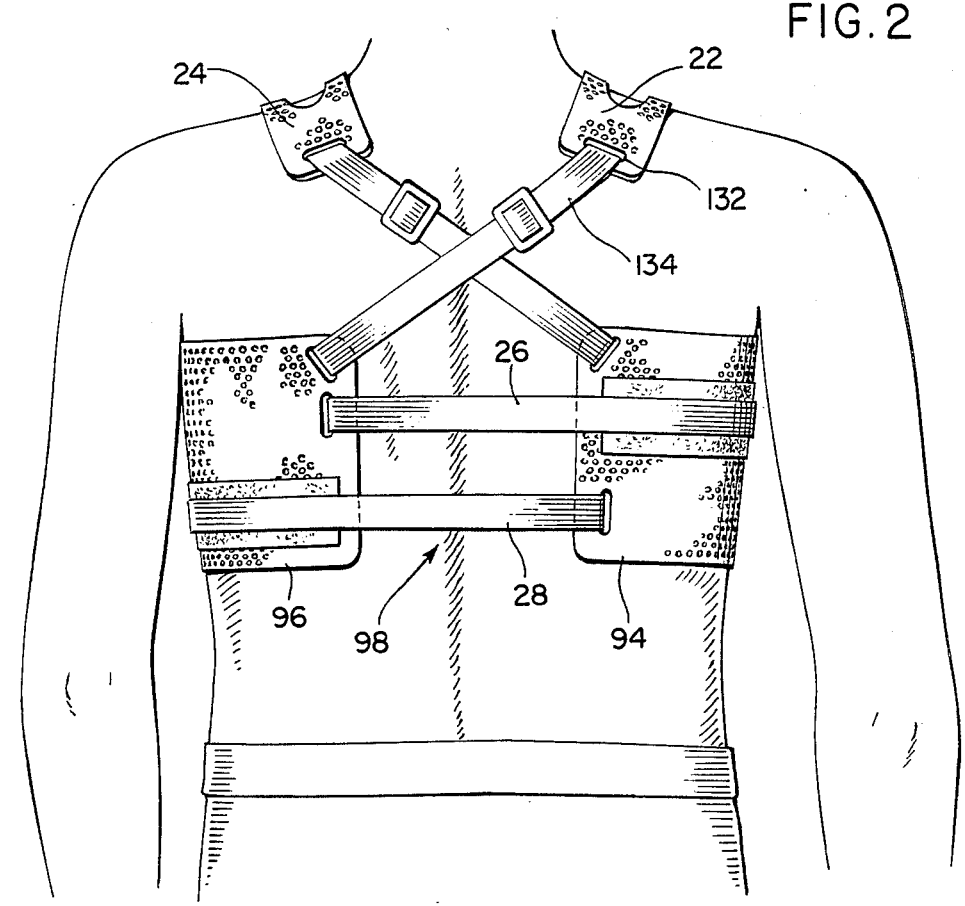
FIG. 2 is a back plan view of the person of FIG. 1 wearing the vest of the subject invention without the electronics package and shoulder strap.

With reference to FIGS. 1-7, the detailed structure of the ambulatory vest will now be described. Basically, the vest 16 consists of a one piece, flexible, thermal plastic material which contains a plurality of ventilation holes 18 arranged in a predetermined pattern to facilitate ventilation between the atmosphere and the skin of the wearer when the vest is in its operative position on the torso as shown in FIGS. 1 and 2. In a referred embodiment, the vest is made from a elastic material sold under the name "Aquaplast".

As shown in FIG. 6, the vest 16 basically comprises an enlarged chest area 92 that fully covers the chest of the wearer, especially in the area of the heart. With reference to its orientation on the torso of a wearer, the lower portion of the vest on either side of the chest terminates in extended strips 94 and 96. Strip 94 passes below the right underarm of the wearer and falls against the small of the back. In like manner, strip 96 passes below the left arm of the wearer and lies against the small of the back. A pair of off-set nylon straps or shoulder supports 24 and 26 are movably positioned within slits 102 and 103 defined on strips 94 and 96, respectively. Each of the straps is secured to the edge of a strip by a series of stitches 104 and terminates in an array of Velcro hooks 106 that mate with a complementary array of Velcro eyes 108 provided on the opposite side of one of the strip portions.

As shown in FIG. 2, the straps pass across the back of the wearer to the Velcro fastener located on the opposite strip in order to securely fasten the vest to the patient. Located along a diagonal, at the front of the vest is an emergency separation or release 110 which is created by holding mating sides 112 and 114 of the vest in an abutting relationship and joining them together by a elastic tape or Velcro 116 that is arranged perpendicular to the orientation of the separation line 115. Strategically placed guides or planar tabs 113, which are secured to side 114, and guide strip 117 which spans the full length of and is secured to strip 114 facilitates placing sides 112 and 114 in abutting relationship. Should the wearer experience any distress during the use of the physiological evaluation system, the vest can be quickly released and easily removed through use of the emergency separation 110, which extends diagonally from the right side of the sternum or breastbone near the persons neck downwardly and away from the stomach area toward the right side of the wearer's body. Also defined on the front of the vest are two large apertures 34 and 36 which define open areas in the 4th and 5th intercoastal spaces for placement of ECG electrodes in conventional manner. The bottom periphery 91 of the vest terminates above the right chestwall of the wearer to permit ready placement of the ground ECG electrode.

In order to prevent the vest from moving vertically up and down, the pair of shoulder straps 22 and 24 are provided. Each of the back straps has the same basic configuration with one strap being the mirror image of the other. The straps are generally shaped like an elongated triangle, with the base portion 122 having a hole 124 on one side and a slot 126 on the other side. The hole and slot are positioned relative to each other so that they mate with threaded lugs 125 and 127 defined along the upper portion of both sides of the front of the vest. The other end 128 of the strap terminates in a slot 132 which receives a belt 134 that is placed in a mating relationship with a slot 138 defined at the end of strip 94. Also defined in the strap near the forward end is an aperture 142 configured to reveal a sufficient portion of the skin of the patient in order to receive a conventional ECG electrode. Thus, straps 22 and 24 provide spaces for mounting the two clavicle ECG electrodes.

On the front of the vest, in the area covering the heart, are four vertically oriented slots 151 through 154. The placement of the slots on the front of the vest is determined in the following manner. The front of the vest may be divided in half along the sternum or breastbone of the wearer. The four slots are defined along the left side of the vest with reference to the sternum. About five inches to the left of the sternum and near the nipple area of the wearer, the vest contains a center point 156. The slots 151–154 exist along a line positioned at about a 10° angle relative to the horizontal plane H through the center point 156. Each of the slots is approximately one inch in length. The slots are oriented perpendicular to the 10° line that is defined through the center point 156. Alternate pairs of slots 151–153 and 152–154 are approximately 6.76 inches from each other as measured along a line parallel to the 10° line. The longitudinal axes of slots 151 and 154 are essentially parallel to each other.

As will be described in greater detail hereinafter, slots 151 through 154 are used in connection with the detector mounting bracket 30 to properly position the cardiac monitor 11 and auxiliary detector 14.

The Detector Mounting Bracket

Figure 3:
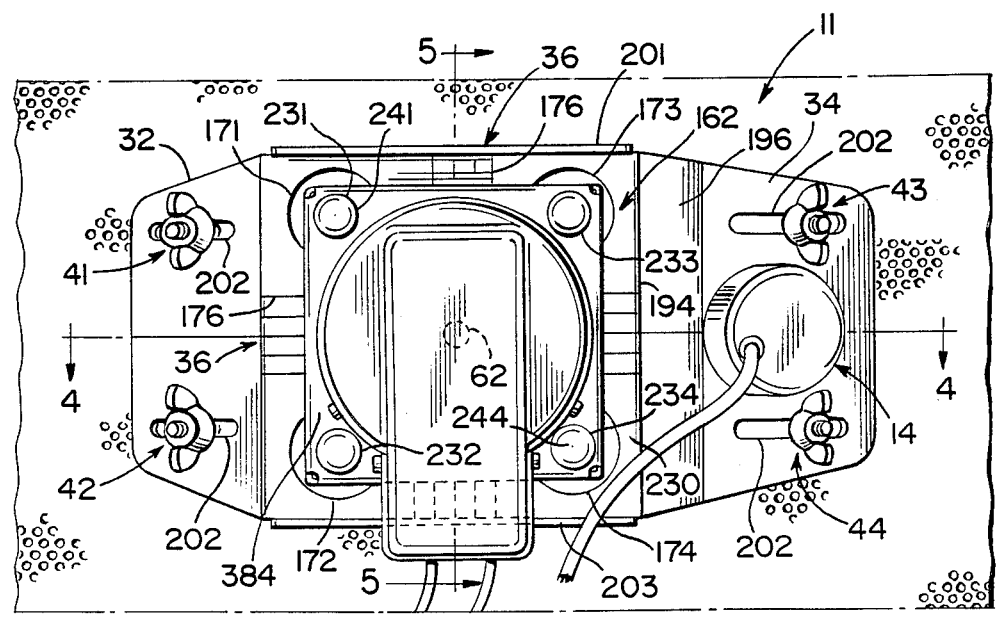
FIG. 3 is a front plan view of the cardiac monitor and mounting bracket for the evaluation system of FIG. 1.

FIGS. 1, 3, and 4 show the detector mounting bracket 30 in its position of intended use and mounted on the vest 16. The bracket is made from a thin aluminum strip and basically consists of a generally square planar mounting face 162 and a pair of planar mounting flanges 32 and 34. Defined at the center of the planar face 72 is an aperture 62 which defines a locating hole used in conjunction with the locating pin 60 of a detector alignment fixture 50. Also defined at each of the corners of the planar surface are larger apertures 171 through 174. Positioned between adjacent apertures along each of the edges of the planar surface are engraved lines 176 which are typically spaced 5 millimeters apart and define scale 36. These lines are engraved on the surface 162 and are used in conjunction with complimentary marks 178 provided on side faces 251 of the main detector 12 in order to properly align the main detector relative to the heart of the wearer.

FIG. 4 shows a toe view of the mounting bracket secured to the vest with the cardiac monitor assembly 11 being secured to the mounting bracket. The bracket 30 has the rear of planar face 182 generally flush with a portion of the vest 16 so that the planar face 162 is generally perpendicular to a line L that passes through a plane P defined along the sternum of the wearer at an angle of approximately 40° to 50° with an angle of 45° being typical. This position is also referred to as the 45° left anterior oblique (LAO) position. The outward planar surface 162 of the mounting bracket terminates in an edge 192 that continues in a planar portion 184 which is at an approximately 90° angle to the plane 162. The end of planar portion 184 terminates in the flange 32 which is at an approximately 48° angle with reference to the planar portion 72. The opposite edge 194 of the planar surface 162 meets with a planar portion 196 that is at an approximately 38½° angle with regard to the planar surface 162. Planar portion 196 terminates in the flange 34 which is formed at an angle of approximately 14½° with regard to the planar surface 162. Both of the flange portions 32 and 34 contain spaced slots 202 which are arranged so that when the detector mounting bracket is positioned on the vest, the longitudinal axes of slots 151 through 154 are generally perpendicular to the longitudinal axes of slots 202 defined on the mounting bracket. In it intended that the mounting bracket be secured to the vest through a series of wine nut assemblies 41 through 44. Each of the wing nut assemblies is made up of a wing nut 212 and a threaded portion 214 that terminates at its end in a flat disk 216 which is flush against the interior surface 218 of the vest when the wing nut assemblies are mounted. The arrangement of the slots 151 through 154 and 202 permit complete two dimensional freedom in positioning the detector mounting bracket relative to the vest.

In an alternative embodiment of the detector mounting bracket (FIG. 8), the planar position 184 is divided up into two overlapping sections 602 and 604 which may move relative to each other to alter the distance from the face 162 to the vest 16. The overlapping sections are held together by wing nut assemblies 606. At the opposite side of the mounting bracket, flange 34 meets portion 196 through a hinge 610. In this way, the mounting bracket may be securely fastened with the face 162 at several different mounting angles without placing any bending stress on the mounting bracket.

Construction and Mounting of the Main and Background Detectors

As shown in FIGS. 3–5, the main detector 12 is mounted within a housing 330 that has a lower portion 332 generally in the shape of a cylinder and an upper portion 334 generally in the shape of an elongated rectangular solid. The housing is made up of upper and lower shells 336 and 338 which are joined together through appropriate fasteners 340 such as pan screws. Two photo multiplier tubes 344 and 346 are positioned next to each other within the upper housing. The operative ends of the photo multiplier tubes are in intimate contact with a light guiding prism 348 made of leaded glass. The lower or cylindrical part of the housing has a cover elate 350 made of black nylon which is screw mounted onto a cylindrically shaped shield 352. The planar surface of the cover plate defines a detecting plane. The part 354 of the shield which receives the cover is of narrower diameter than the remaining portion 356 of the shield. In a preferred embodiment, the shield is made cf lead with 5% antimony. Positioned next to the cover is an iris 358 made up of a thin sheet 360 of spring tempered aluminum and a metal ring made from lead with 5% antimony. The iris is optionally used to restrict the field of view in the case of a child's heart or a small adult heart. Positioned next to the iris is a lead collimator 364 having an array of gamma ray guiding tubes 366. The other side of the collimator is adjacent a sodium iodide (NaI) crystal assembly 368. Between the collimator and the crystal assembly is a rubber protective gasket 370. A guide ring 372 made of lead with 5% antimony is in intimate contact with the lead shield. The guide ring receives and holds a leaded glass window 374 adjacent the NaI crystal. Between the glass window 374 and the NaI crystal 368 is a very thin layer 375 of epoxy or an RTV silicon rubber. The top of the glass window is in communication with one side of the light prism 348. A connector 380 having a built-in voltage divider and preamplifier is connected to the photo multiplier tubes. The cable 383 is connected to the other side of connector 380 and emerges from the housing 338 for connection with the circuitry in bag 80.

A generally hollow aluminum monitor base 230 completes the construction of the main detector. The base has a planar square surface 384 within the center of which is defined a large circular aperture having a diameter sized to receive the narrower portion 354 of shield 352. Also defined within the surface 384 are four mounting holes 231-234. Further details of the construction of the main detector 12 may be found in copending Suzuki U.S. patent application Ser. No. 711,096 for High Energy Radiation Detector and Method of Detection, which is incorporated by reference.

The way in which the main detector 12 is fastened to the detector mounting bracket 30 will now be described with reference to FIGS. 3–5. In connection with mounting the main detector to the mounting plate, use is made of a floating base plate 76 which may be movably retained to the mounting bracket 30 by a suitable means such as a spring or tape. The base plate is generally square in configuration with flattened or rounded edges 222 at the corners. At the center of the base plate is an aperture 224 which is of larger diameter than the aperture defined in the mounting plate. Located at each of the corners is a stand off, 71 through 74, which has a vertical axis oriented perpendicular to the planar surface 226 of the base plate. Each of the stand-offs is internally threaded. The base plate, like the mounting bracket is made of aluminum and is positioned behind the planar surface 162 of the mounting bracket in the space defined between the outer surface 228 of the vest and the interior surface 182 of the bracket face so that each of the stand-offs protrude through one of the enlarged apertures 171-174. At the same time, the planar face 226 of the base plate is in intimate contact with the interior face 182 of the mounting bracket. The main detector 12 is supported on base 230 which contains apertures 231-234 in each of the corners of the base in order to receive the stand-offs 71 through 74 of the floating base plate. A knurled, threaded lug 241 is then used to secure the base plate and the main detector to the mounting bracket. With reference to FIGS. 1 and 3, it can be seen that the main detector 12 on the base 230 contains four side faces 251, each of which bears index mark 178 which is brought into registry with one of the scales 36 defined about periphery of the surface 162 of the mounting bracket. In this way, the main detector may be mounted anywhere on the surface 162 within plus or minus 10 millimeters since each of the scale gradients 176 on the surface 162 are 5 millimeters apart.

Figure 15:
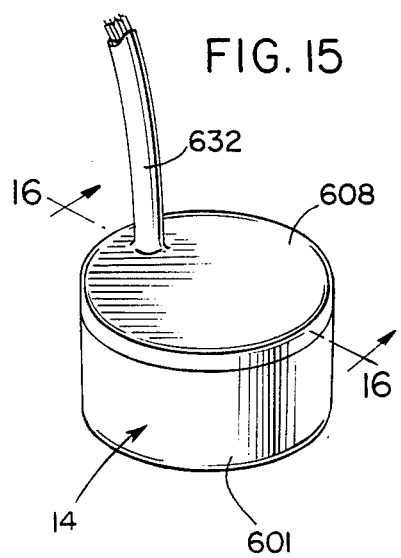
FIG. 15 is a perspective view of the auxiliary detector used in the evaluation system of FIG. 1.
Figure 16:
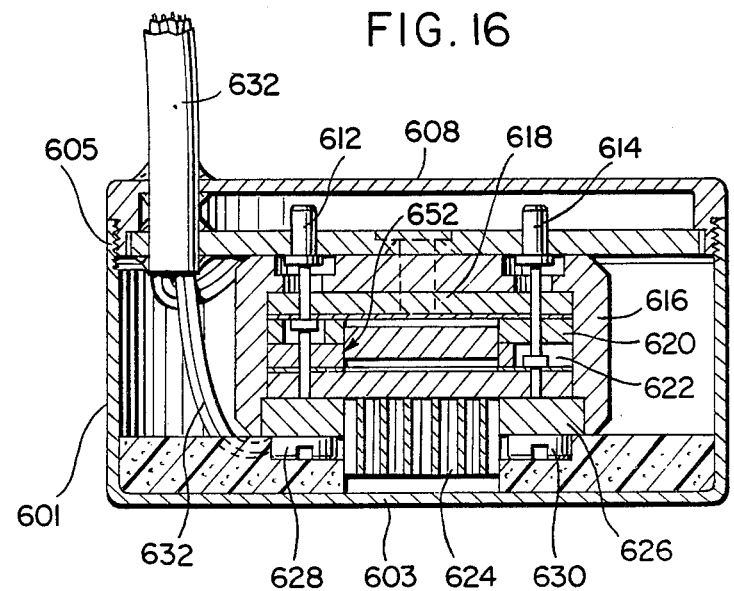
FIG. 16 is a view taken along lines 16—16 of FIG. 15.

With reference to FIGS. 3, 15, and 16, the construction and mounting of the auxiliary detector will now be described. The auxiliary detector includes a cylindrically shaped case 601, the floor of which defines a face 603 for the detector. The opposite end of the case contains a threaded portion 605 which mates with a complimentary threaded portion on a cover plate 608. Together, the case and the cover plate define a housing within which is mounted the CdTe detector. Positioned within the housing near the cover 608 is a printed circuit board 610 which contains the preamplifier circuitry associated with the detector. Mounted in the circuit board are extended pin contacts 612 and 614. Next to the underside of the circuit board is a cylindrically shaped hollow lead shield 616. Positioned within the shield is an insulator board 618 and alternate carrier boards 620 and 622. The carrier boards define a square portion 652 which houses a CdTe chip. The bottom portion of the shield receives a cover 626 which has a circular shape to receive a honeycomb collimator 624. At the underside of the cover, near the bottom of the case, are contact mounting lugs 628 and 630 which receive leads 632. The leads emerge from the cover of the housing for connection to the data logger that is contained in the bag 80. The conductive contacts 612 and 614 provide electrical contacts with the CdTe chip through the carriers 620 and 622.

Since the detector may be used on various parts of the body, it is desirable to be able to replace and easily remove the detector as desired. In a preferred embodiment, the face 604 of the detector may be coated with a double stick tape so that the auxiliary detector may be placed as shown in FIG. 3, on the detector mounting plate or in other locations on both the body and the vest.

Location of the Cardiac Monitor

In order to get the most accurate readings from the cardiac monitor, it is imperative that the optimum position of the main detector relative to the left ventricle be determined and maintained during the detecting period. Thus, as part of the present invention, a structure and method are provided for determining the exact location of the left ventricle and positioning the mounting bracket so that precise placement of the main detector may be insured.

As has already been described, the main detector 12 is secured to the vest through the use of a mounting bracket 30. In a preferred embodiment, the bracket is a light weight formed metallic structure with a series of slots 202 for attaching the bracket to the vest and a series of enlarged apertures 171-174 for mounting the cardiac monitor. Thus, it can be seen that the bracket may be adjustably mounted to the vest and the main detector may be adjustably mounted to the bracket thus providing adjustment of the main detector relative to the left ventricle of the heart within two degrees of freedom.

An alignment fixture 50 is employed in order to properly align the detector mounting bracket relative to the vest. The alignment fixture is generally illustrated in FIGS. 9-14. The purpose of the fixture is to transfer a location of an anatomical body, such as the left ventricle of the heart, utilizing a conventional scintillation camera.

Figure 9:
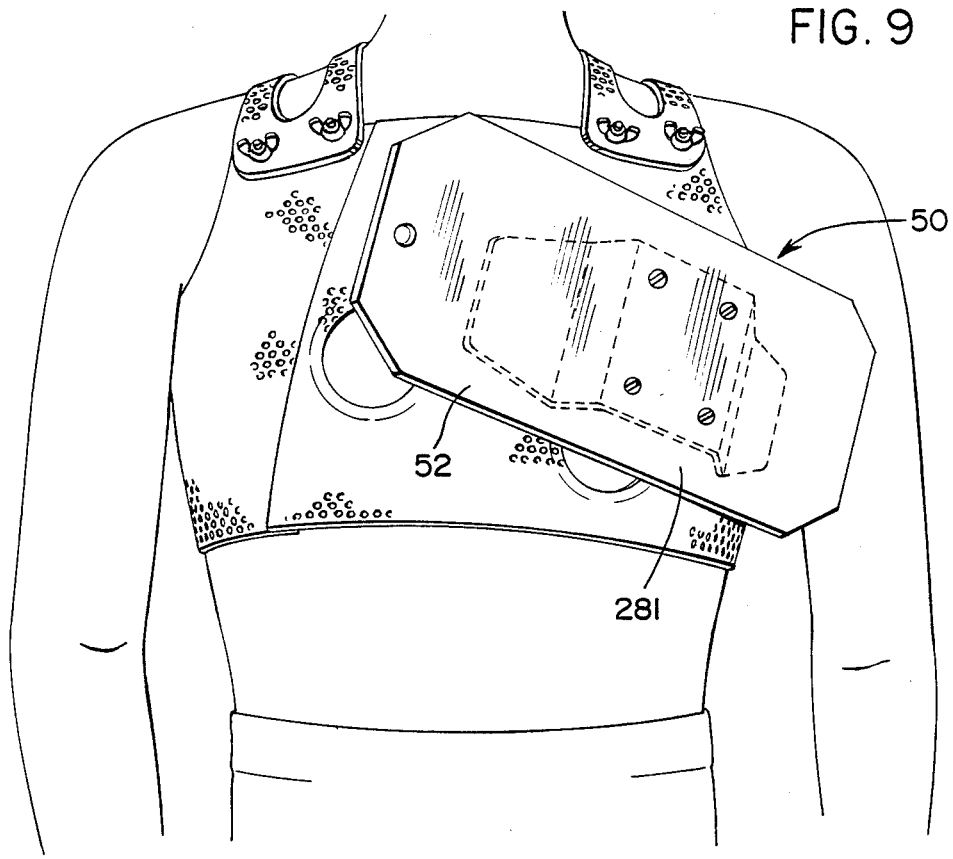
FIG. 9 is a front perspective view of the vest of FIG. 1 with the alignment fixture in place on the detector mounting bracket.
Figure 14:
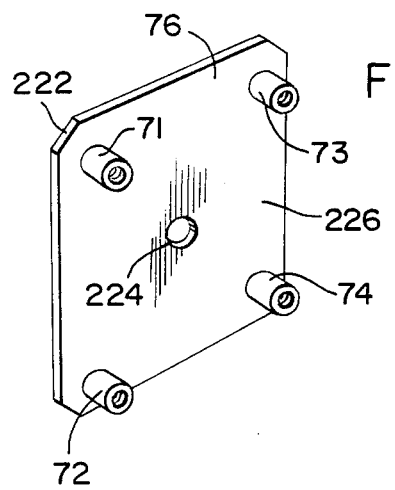
FIG. 14 is a perspective view of a floating base for use mounting items on the detector mounting plate of FIG. 3.
Figure 10:
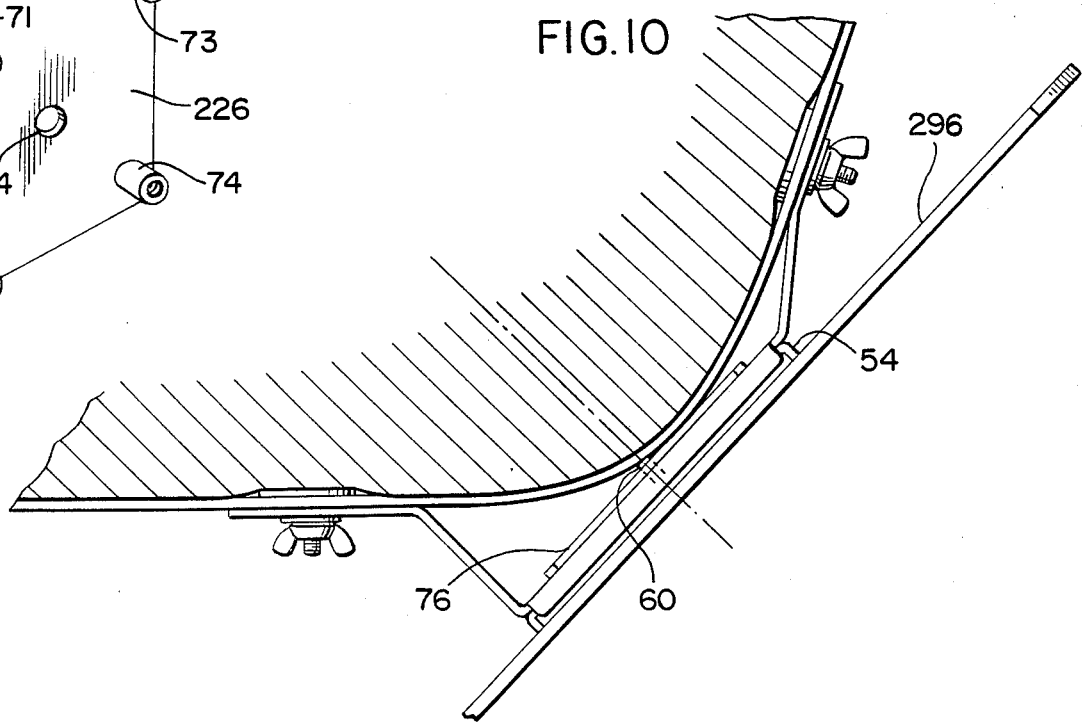
FIG. 10 is a top view of the arrangement of FIG. 9.
Figure 11:
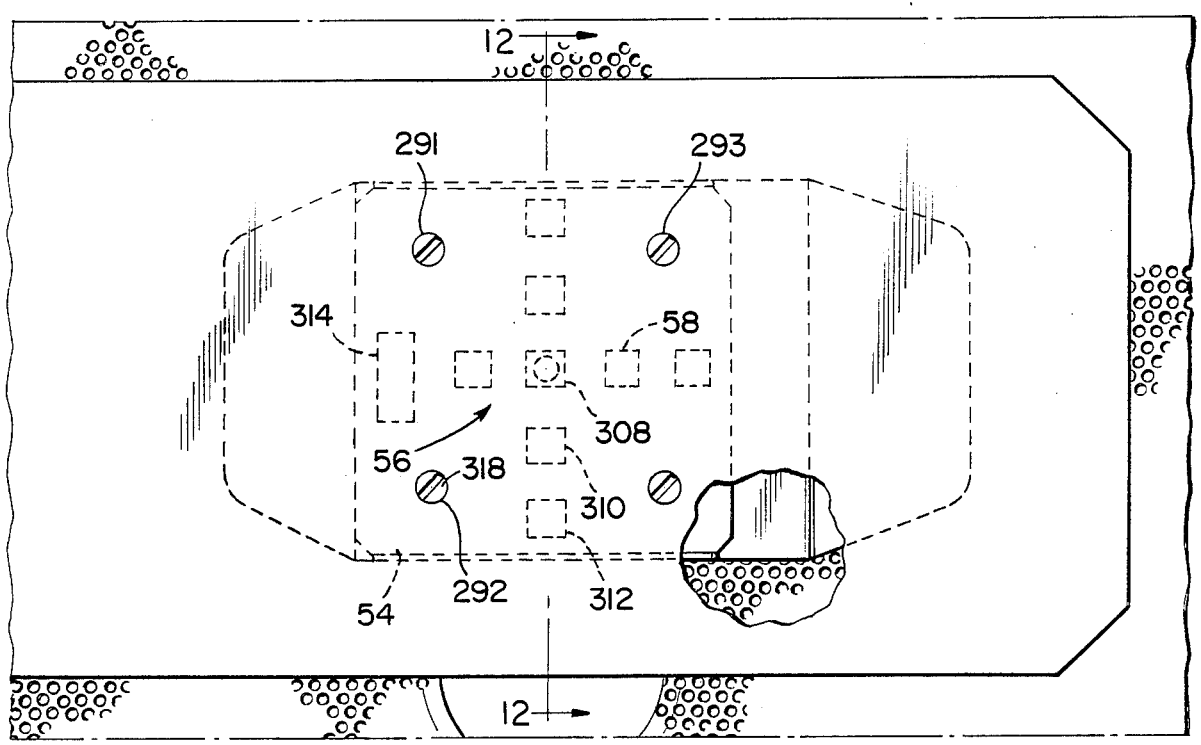
FIG. 11 is a elan view of the alignment fixture of FIG. 9.
Figure 12:
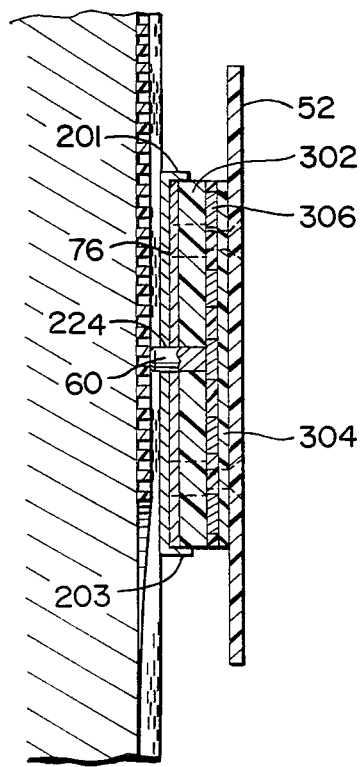
FIG. 12 is a view taken along lines 12—12 of FIG. 11.

With reference to FIGS. 9-11, the alignment fixture may be described as follows. The fixture basically comprises an elongated planar leveling plate 52 on which is mounted a generally square planar cursor-locating plate 54. Both the leveling plate and the cursor plate are preferably made of a transparent plastic material. Defined on one side 281 of the mid-portion of the planar leveling plate are a series of four holes 291-294 aligned to receive the stand offs 71-74 from the floating backing plate 76. Positioned on one surface 296 of the leveling plate is the cursor or centering plate 54 which also contains four apertures that are brought into alignment with the apertures 291 through 294 defined in the leveling plate.

Figure 13:
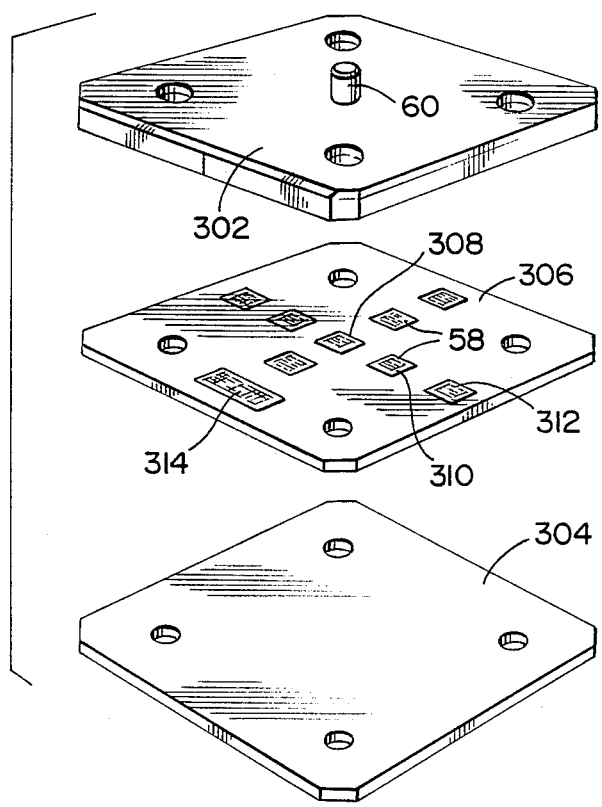
FIG. 13 is an exploded perspective view of an embodiment of the cursor-locating plate.

The cursor plate actually consists of two planar portions 302 and 304. Sandwiched between these surfaces are an array of lead cursors 58 which aid in aligning the detector mounting bracket relative to the left ventricle of the heart. As shown in FIG. 13 the lead cursors generally consist of lead slugs which are one mill meter thick and 10 millimeters on a side. The slugs are arranged within evacuated areas defined on a middle layer 306 in a cross with one cursor 308 being at the center of the cross and two cursors 310 and 312 being on either side of the center cursor on the legs of the cross. Together, the cursors define a centerline. All of the lead cursors are the same size with the exception of the cursor located on the left as shown in FIG. 11. This cursor 314 is 10 millimeters by 20 millimeters and acts as a direction alignment cursor to identify left and right on any image that includes the cursor. It is to be understood that the three layer construction of the cursor plate is for a preferred embodiment and other methods of construction will readily suggest themselves to those skilled in the art.

Emanating from the central portion of the housing is locating pin 60. This pin is brought into registry with the aperture 62 defined in the mounting bracket. At the same time, suitable fasteners such as screw 318 are used to fasten the leveling plate and the housing to the mounting bracket by passing the fastener through the apertures defined in both the leveling plate and the housing. The screws are then secured to the threaded studs provided on the floating backing elate. The detector alignment fixture is now centered on the detector mount.

A conventional scintillation or gamma camera (not shown) is brought up to the alignment fixture and adjusted so that the recording plane of the camera is parallel to the face 281 of leveling plate 52. The cathode ray tube display for the scintillation camera shows the position of the lead cursor array 56 relative to the shadow of the left ventricle of the heart. If the center line of the cursor array is within 10 millimeters of the desired position of the left ventricle of the heart any further adjustment can be made with the detector mounting bracket as described hereinbefore. In this case, the alignment fixture may be removed and replaced by the main detector 12. If the location of the center line of the cursor is further away from the desired portion of the left ventricle then 10 millimeters, the mounting bracket must be readjusted relative to the vest and the above procedure repeated. The adjustment range of the alignment fixture and the mounting bracket may be altered by changing the distance between gradations on scale 36.

In a preferred embodiment of the subject invention, there is a specific alignment procedure in order to mount the cardiac monitor relative to the vest and in that way position the cardiac monitor at a certain location relative to the left ventricle of the heart.

Initially, a vest which fits the patient is selected. The detector mounting bracket 30 and the floating base plate 76 are secured to the vest. The vest is then placed on the patient and the straps are adjusted to eliminate movement of the vest relative to the body of the patient. The mounting bracket is adjusted so that it is proximately near the heart, some 40° to 45° clockwise using the sternum or breastbone as a center line. As in the case of the vest, a mounting bracket appropriate for the patient's body structure is selected.

The floating base plate 76 is positioned so that the studs 71-74 of the base plate emerge through the large diameter holes 171-174 defined in the mounting bracket. The alignment fixture is aligned so that the long end of the fixture points to the right side of the patients body (when looking at the patient's face). The center pin 60 of the alignment fixture engages the center hole 62 of the mounting bracket. The alignment fixture is then secured to the detector mounting bracket through the captive fasteners.

The gamma or scintillation camera is then positioned parallel to the force of the alignment fixture and as close as possible to the leveling plate. The gamma camera is activated in order to observe the position of the center ling of the alignment fixture relative to the left ventricle of the heart. If the center of the alignment fixture is within 10 millimeters of the center of the left ventricle then the gamma camera is removed along with the alignment fixture. The cardiac monitor is then mounted to the camera mounting bracket.

If the center of the alignment fixture is greater than 10 millimeters away from the center line of the left ventricle, then the fasteners between the mount and the vest are loosened and readjusted to reposition the camera mounting bracket and thus alter the position of the center line so that it is within the 10 millimeters required.

Electronics and Information Processing System

Figure 18A:
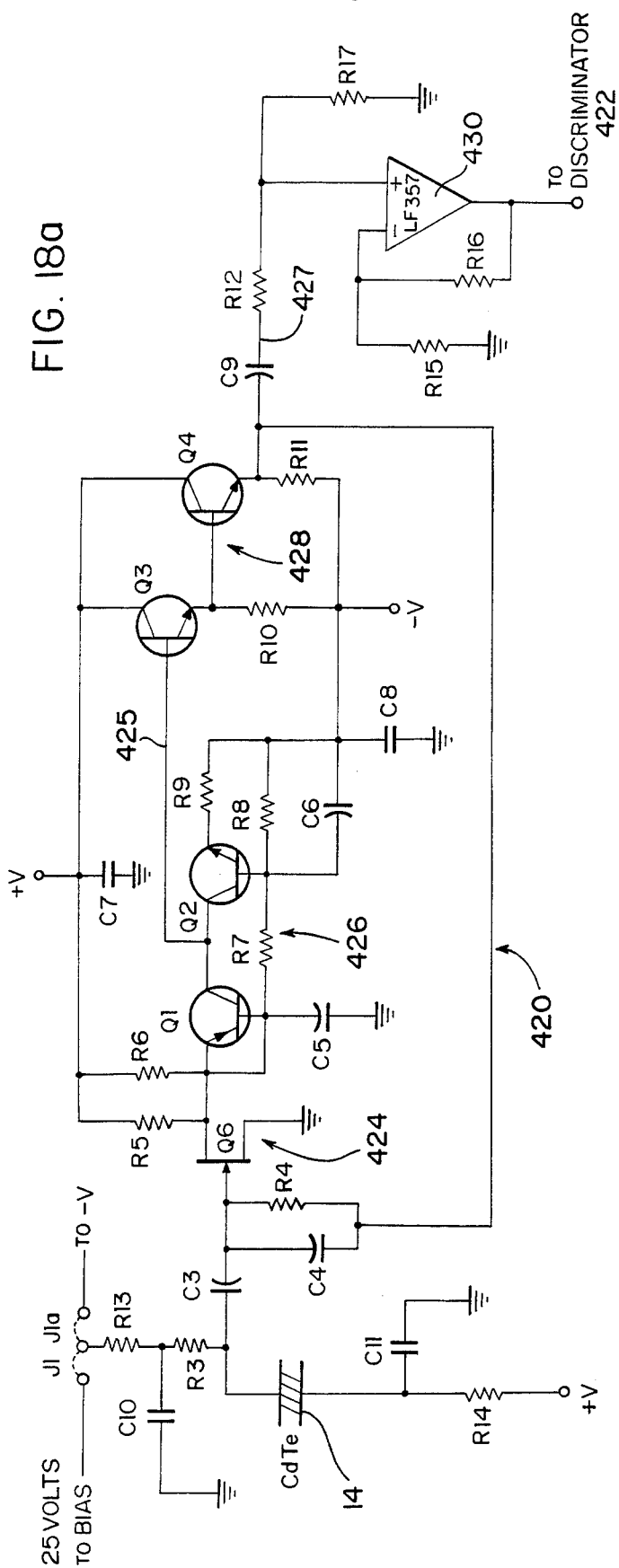
FIG. 18a is a schematic diagram of a charge coupled amplifier used in the electronic portion of FIG. 17.
Figure 18B:
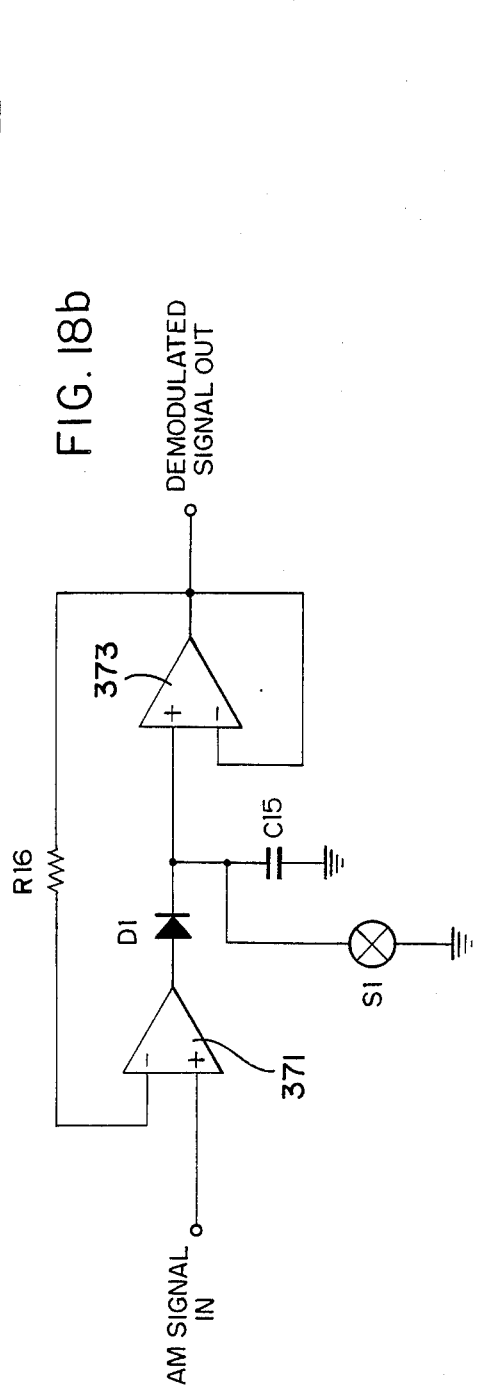
FIG. 18b is a schematic diagram of a positive peak hold circuit used in the electronic portion of FIG. 17.

Also forming part of the ambulatory ventricular evaluation system are several electronic components. With reference to FIGS. 17, 18a and 18b, a preferred embodiment of the evaluation system basically comprises a Cadmium Telluride (CdTe) detector which is used as the auxiliary detector 14 that is responsible to the presence of a suitable radiopharmaceutical, such as TC-99m tagged red blood cells, injected into the circulatory system to provide an output signal representative of the left lung time activity. The CdTe detector assembly 14 consists basically of a CdTe detector 640, a radiation collimator 624, a radiation shield 616, and a preamplifier. A cardiac monitor 11 that includes the main detector 12 is also responsive to the presence of a suitable radiopharmaceutical injected into the circulatory system, produces a signal which is proportional to the energy level of radiation emitted by the radiopharmaceutical over the cardiac cycle. The signal produced by the main detector is representative of the left ventricular time activity of the heart. Both of these signals are fed in analog pulse form to a data logger, which is housed in a bag 80 worn by the patient. The data logger includes the circuitry necessary to accumulate and manipulate the data and transfer it to a portable cassette recording device 82 also housing in the bag. Also, feeding information into the recording device are conventional EKG electrodes 84. After the information has been recorded over a desired period of time, the recorded information is presented, through an a tape player 87, interface 86 and an A/D converter 88, to the memory 90 of stand along computer 92 located in a hospital or office for later processing and analysis.

At the heart of the electrical system is a microcomputer 450. In a preferred embodiment, the microcomputer is one produced by National Semiconductor and bears the product designation MA2800. The microcomputer is a low power, eight bit CMOS microcomputer system. It provides a central processing unit, read only memory 451, random access memory 453, parallel and serial input/output ports, a system clock, programmable timers, and priority interrupt logic. The microcomputer is used to control the timing and operation of the other circuitry associated with the ambulatory evaluation system in the manner explained hereinafter.

FIGS. 17 and 18a show in greater detail the electronic circuitry associated with the ambulatory ventricular evaluation system. A series of Nickel Cadmium batteries 401 provide a voltage and current to a voltage regulator 402 in order to provide a regulated 5 volt DC supply 404. The 5 volt regulated supply is used to power up the various circuit elements that make up the evaluation system. In addition, the 5 volt supply powers up a high voltage power supply 406 in order to produce a 1000 volt D.C. signal which is used in conjunction with processing the outputs from the two photo multiplier tubes 344 and 346 found in the cardiac monitor 11. The outputs from the two photo multiplier tubes are passed through a high speed, charge coupled amplifier 408 and then into the negative input as a comparator 410 for discriminating signals. A more detailed discussion of the way in which the cardiac monitor operates to produce the signal that emerges from charge coupled amplifier may be found in aforementioned U.S. patent application Ser. No. 711,096, which has already been incorporated by reference herein. The positive input of the comparator receives a predetermined reference signal which is typically set at 300 mv. Whenever the output of the high speed charge coupled amplifier exceeds the reference signal, the comparator 410 triggers a one shot multivibrator 412 which further shapes the signal into a four microsecond pulse for introduction into a 16-bit counter 414 which is part of the microcomputer 450.

As stated before, the auxiliary detector 14, which is a CdTe detector is positioned in an appropriate location for intended study. As shown in FIG. 3, the detector is adjacent to, and to the left of the cardiac monitor 11 on the ambulatory vest 10. The auxiliary detector 14 produces a signal representative of time activity of the area selected for study. With the detector positioned as shown in FIG. 3, the signal produced is representative of left lung time activity. The signal is passed through a charge coupled amplifier 420 and then into a signal discriminator 422. The operation of the charged coupled amplifier may be described as follows. The charge coupled amplifier is composed of transistors Q1 through Q4. The CdTe detector 14 which is biased to 25 volts, produces a charge which is collected at capacitor C4. From there, the signal passes through the front end of the charge coupled amplifier 420 which is a low noise FET amplifier Q6. The output of the FET passes through transistors Q1 and Q2 which are configured as a high impedance constant current load to generate an amplified pulse on lead 425. The amplified pulse is fed into the input of a Darlington amplifier made up of transistors Q3 and Q4. The output of the Darlington amplifier passes along lead 427, through capacitor C9 and resistor R12 into a voltage amplifier 430 which produces an output signal of about 40 to 100 millivolts. The discriminator 422 is used to convert the output of the charged coupled amplifier into a pulse signal for input into a 12-bit counter 432. Whenever the input into the comparator 434 exceeds the reference signal of about 15 to 100 mv, the output of the comparator is passed to a multivibrator which has been configured as a trigger 436. Every 32 milliseconds, the microcomputer takes the nuclear data information contained in the 16-bit counter and passes it along the data bus 440 to a digital-to analog converter 442 in a sequence to generate an amplitude modulated signal as described below. The counts generated by the background detector are accumulated in a 12-bit counter 432 for 8 consecutive one second periods. The average of these one second counts is then outputted to the tape recorder on a second track in the format describd below. Since the background count is only one of eight possible ditigal channels the data for each channel is stored and outputted in serial form in the allotted one second slot.

Analog Digital Recording

In the ambulatory cardiac evaluation system of the present invention large quantities of data must be recorded on suitably memory media and subsequently retrieved for analysis. The nature of the information that is to be recorded has both A.C. alternating current) and D.C. (direct current) components. Therefore, straight analog recording is not possible because a conventional tape recorder does not reproduce the D.C. components. In accordance with the present invention, the information is recorded on two tracks of the tape recorder. One track records the analog information from D/A converter 442 in an Amplitude Modulation format and the other track records the digital average of the analog signal in digital format. Before this is done, the microcomputer 450 samples the analog signals produced by either the auxiliary detector 14 or the main detector 12 above the Nyquist rate. Using the signal from the main detector as exemplary, the microcomputer generates an average digital value based on the previous n samples. The number of samples n over which the average is taken is suitably selected so as to optimize the overall frequency response of the signal. This digital value is recorded on one of the channels of the multichannel tape recorder 82.

Each of the digitized values of the sampled analog signal is then presented to a D/A convertor as a positive magnitude corresponding to the value followed 16 ms later by an equivalent negative value. In effect, this is amplitude modulation (A.M.) performed in software. An enhancement technique is employed to improve the signal to noise ratio, whereby a fraction of the average count for the last measurement is subtracted from the current count sample from counter 414. The counting time period determines the carrier frequency of the amplitude modulation.

Figure 20:
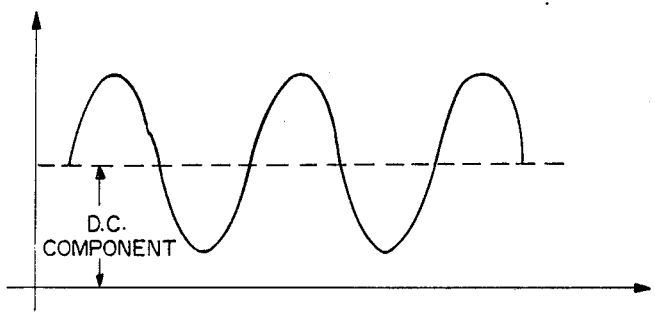
FIG. 20 is a waveform used in explaining a portion of the operation of the electronic portion of FIG. 17.
Figure 21:
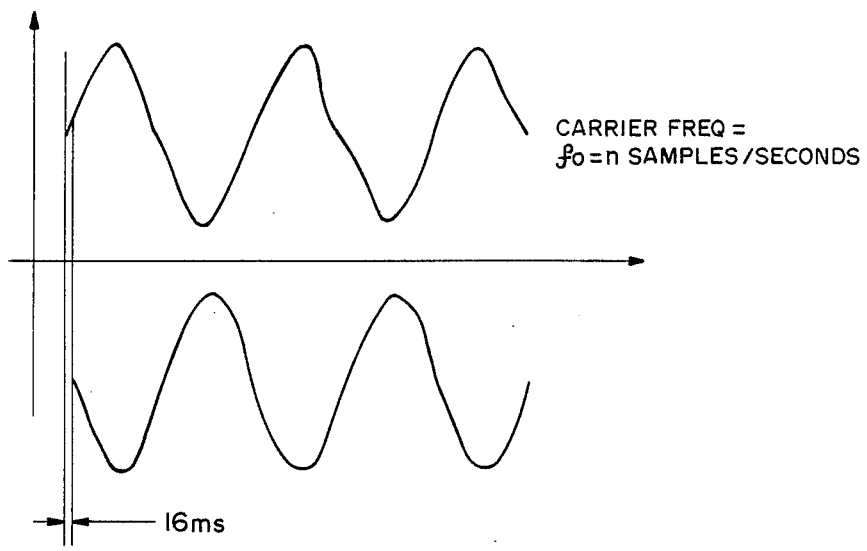
FIGS. 21 and 22 are waveforms used in explaining a portion of the operation of the electronic portion of FIG. 17.

For the purpose of explaining how the data sampling technique is applied to the inventive ambulatory physiological evaluation system, assume that there are n samples/second. For the sake of clarity, also assume that these samples represent a signal that is a sinusoidal wave offset by a D.C. value. The graphic representation of this signal after passing these signals through D/A convertor 442 is shown in FIG. 20. If this analog signal were presented to the magnetic tape recorder, the D.C. value would be lost because of the limited bandwidth of the recorder. FIG. 21 shows the same digital sample processed through the D/A convertor with each digital sample being presented as a positive magnitude followed by the equivalent negative magnitude after a time delay of 16 ms. The result is an amplitude modulated wave.

Figure 22:
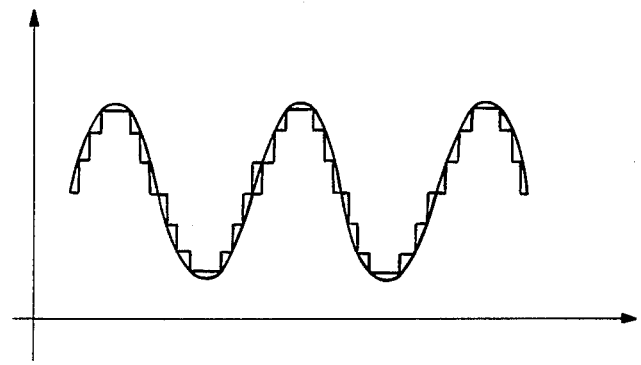

Applying this signal to the magnetic tape recorder in which the carrier frequency $f_0$ lies well within the mid-band of the frequency response of the recorder allows full transcription of the A.M. signal. The original signal can be recovered by application of standard demodulation techniques. The demodulated signal is digitized by an analog-to-digital converter and then recorded in the memory 90 of the computer 92. The low frequency component (D.C. level) obtained from the digital recording is then added to obtain full reconstruction of the original count from counter 414. The demodulator used in a preferred embodiment is a positive peak hold circuit and is shown in FIG. 18b. The demodulation is formed as part of the computer 92. The demodulator basically comprises two operational amplifiers 371 and 373. The negative inputs of each amplifier are connected to each other by way of resistor R16. The positive input of amplifier 371 receives the A.M. signal. The output of amplifier 371 passes through diode D1 and into the positive input of amplifier 373. The output of amplifier 373 is fed back to the negative input of amplifier 373 and also defines the output for the demodulated signal. The positive input of amplifier 373 is connected to ground by way of the parallel arrangement of switch S1 and capacitor C15. Each positive peak is held by capacitor C15 until the next positive transition through zero at which point the capacitor charge is dumped via switch S1 which is controlled by computer 92. The resultant output is shown in FIG. 22. The amplitude of each of the held peaks represents the value of each counting period. These held peaks ultimately are digitized. Since the peaks are held, the exact timing they are digitized is not critical. The process of reconstructing the signal is discussed later.

The frequency of the carrier signal selected is, as mention earlier, also the sampling rate. It should be chosen to exceed the Nyquist rate and also lay in the mid-band of the tape recorder's frequency response. Additionally, the carrier frequency is used to synchronously demodulate the signal later on.

Figure 23A:
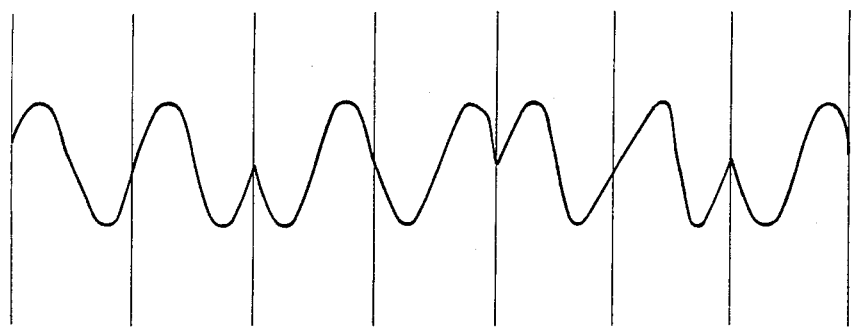
FIGS. 23a–23c are waveforms used in explaining a portion of the operation of the electronic portion of FIG. 17.
Figure 23B:
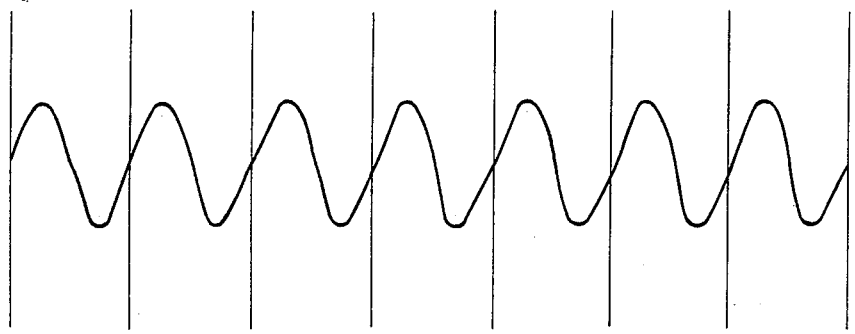
Figure 23C:
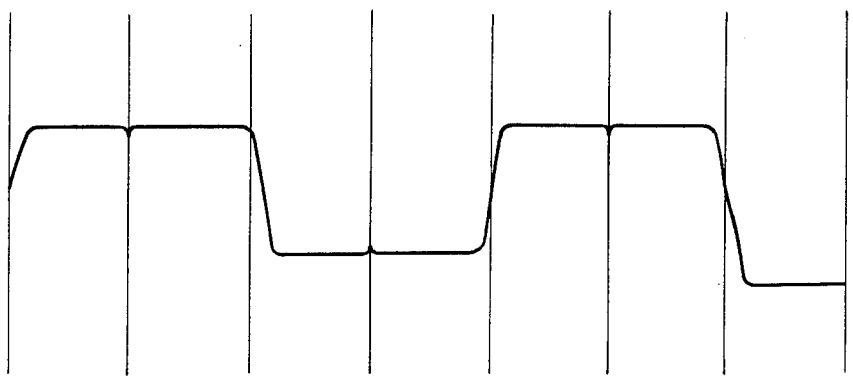

The digital data output is synchronized to the D/A sampling period. This means that every time a D/A operation is performed on a sample, a bit of serial data from the parallel serial register 444 is subsequently put out under the control of gate 431. Again, the output is in a Return-Through-Zero format. This means a "1" is represented as a positive excursion followed by an equal negative excursion and vice versa for a "0". FIGS. 23a–23c show the timing diagram of both D/A and Digital outputs. The digital data uses phase encoding to generate a "1" or a "0". An example of a sequence 1100110 is shown in FIG. 23a. The digital data is synchronized to the D/A output waveform (FIG. 23b). The digital signal can therefore be demodulated (FIG. 23c) by using the D/A signal as a phase reference. The implementation of this phase detection is done using a sample and hold circuit. The digital signal is sampled for the first ¼ cycle of the reference D/A output and held till the beginning of the next cycle as shown. A "1" is represented as positive held voltage; a "0" is represented as a negative held voltage.

In order to make best use of the information obtained from the electronic circuitry associated with the ambulatory physiological evaluation system, the cassette recorder 82 has four tracks capable of recording information. The tape speed is typically 2 mm per second and data from the patient may be recorded for up to twenty four hours. In a preferred embodiment, the frequency response of the recorder is 0.01–100 hertz at the nominal tape speed. Track 1 contains the nuclear analog output, which is in the form of left ventricular cardiac Beat-to-Beat analog data. The information is obtained from the D/A converter at a sampling rate of 32 Hz. The information is recorded on track 1 in an amplitude modulated format.

Track 2 records eight groups of digital data. The data is processed by the microcomputer 450 and may consists of any or all of the following:

average nuclear counts;
average auxiliary counts;
secondary auxiliary counts;
event marker and time;
blood pressure;
temperature; and
pulse rate; etc.

The eight groups of digital data are interleaved and a group is outputted every second. An identifier code proceeds each piece of data so that the data may be separated later on. Parity checks are included in the data for error detection. The format is composed of 16-bits of data, with 2-bits of parity. The rest of the time left in the one second transmission is left as a blank. The blank area is useful in determining the beginning of a new word. Track three of the recorder is dedicated to record one channel of ECG in standard analog fashion. Track four may be used to record the second ECG signal or another physiological signal, such as blood pressure.

Once data has been recorded, the cassette tape is transferred to a four channel audio tape recorder where the data is played back at a speed factor of between 60 and 240. The speed-up is necessary in order to bring the frequency of the ECG recording within the band with of the audio tape recorder. Since ECG normally has a frequency spectrum of between 0.05 and 100 Hz, the speed up ratio of 100 or more is needed.

The carrier frequency of the nuclear data is used in initiate the triggering of a multichannel A/D converter 88. The four channels of the play back recorder are sequentially multiplexed and made available to the high speed A/D converter. The A/D converter transfers the data directly to hard disk by direct memory access. Some filtering and processing of the signals are needed. For these reasons, an anti-aliasing RC filter is required at the output of all four channels.

The digital data acquired on hard disk memory 90 via the high speed A/D converter 88 is sorted out by using tags (identifiers associated with each digital channel), as well as the data sequence itself. Once sorted, the data is compartmentalized and stored as separate files, within the memory of the computer 92. The digital samples representing the nuclear analog signal are summed and averaged over an eight second period. These 8×32 samples are bracketed by two digital channel averages (since one average is recorded every eight seconds). The first digital average is used to reestablish the offsets that were subtracted by the front end. This digital offset was generate to enhance the A/C component of the signal as mentioned earlier. The current average second digital value is used as the normalizing factor for the detector counts.

Evaluation and Manipulation of Data

Figure 19:
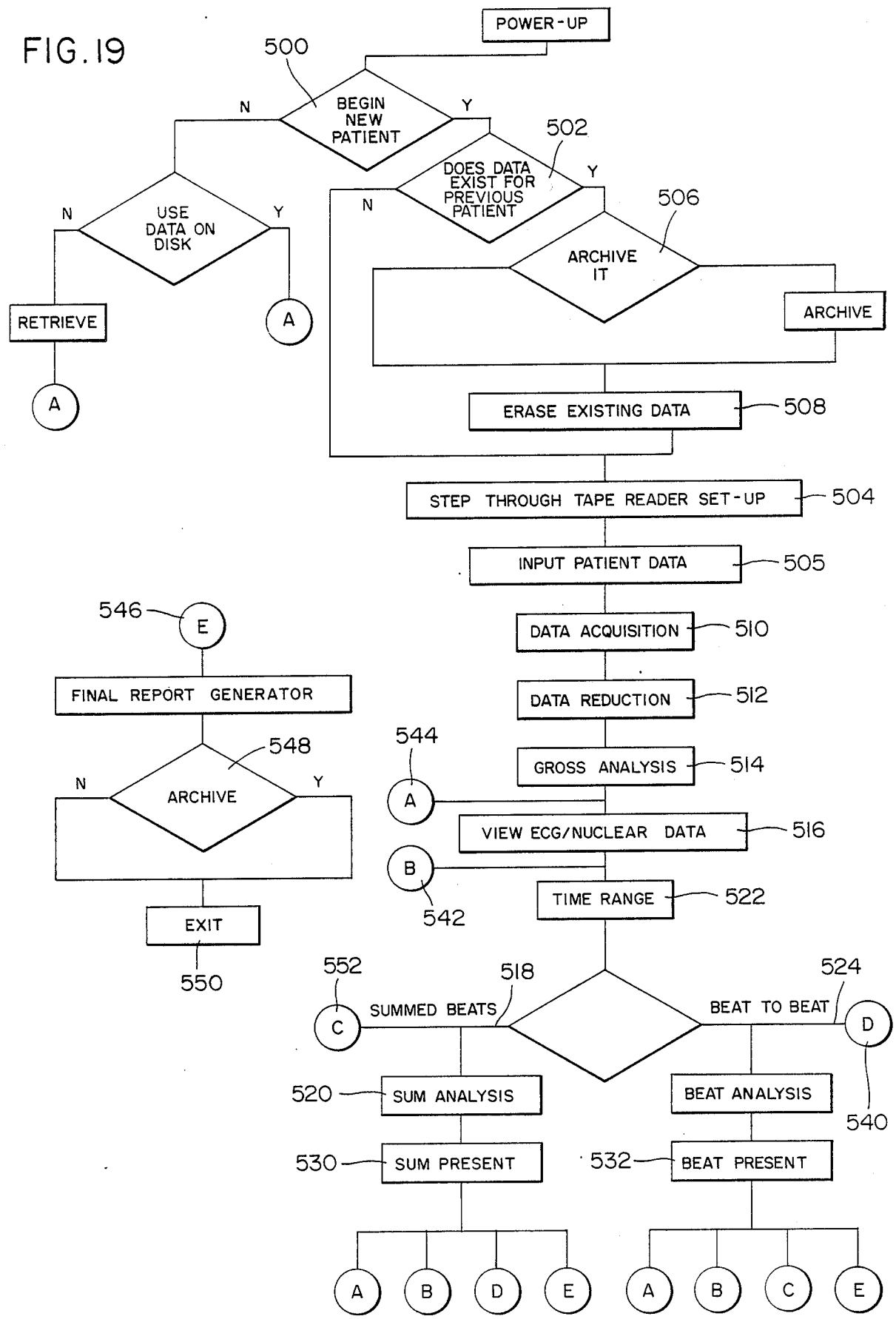
FIG. 19 is a flow chart used to explain the operation of the computer forming part of the evaluation system of FIG. 1.

After the information from the recording device has been unloaded and stored in the memory 90 of the computer 92, the commuter then analyzes and manipulates the data in order to produce a final report. FIG. 19 presents a flow diagram showing the various tasks performed by the software contained in the computer. Initially, the computer is powered up in order to start its operation. A menu appears on the screen with the following choices:
1. Data Acquisition
2. Data Reduction
3. Identify R-waves
4. Input Patient Data
5. View ECG/Nuclear Data
6. Gross Analysis
7. Beat-to-Beat Analysis
8. Summed Beat Analysis
9. Exit Selection of the desired function is made by pressing the appropriate numbered key on the keyboard.

Normally, the first determination to be made is with regard to inputting patient data (505). The computer ask the user whether to begin a new patient (500). If the answer is yes, the commuter asks "Does data exist for a previous patient?" (502). If the answer is no, then the computer proceeds to Step-Through-Tape-Reader-Set-Up (504). In this phase of operation, the user is stepped through the procedure for setting up the computer's tape reader by prompts appearing on the display 91. The system then moves onto the Data Acquisition Step 510, where the data is actually obtained from the cassette tape. Nuclear and ECG data are obtained from the analog to digital converter circuitry and then stored in memory by direct memory access. From the memory, the information is stored on disk. If the answer is yes, the computer goes through an archiving protocol (506) where information concerning the previous patient is obtained from a previously recorded file. Certain of the data is then erased (508) and the user is placed into the Step-Through-Tape-Reader-Set-Up. Average data, background data and other digital data are also read in simultaneously and stored in files on a disk.

The program may then proceed to Data Reduction 512 where the raw data read in and written to the files is converted into usable data. The first aspect of the system program is devoted to the conversion of nuclear data to counts. With regard to ECG data, the program finds each R-wave peak through the use of look-up tables. R-wave peaks and R-to-R intervals are written to a file.

After data reduction has been completed, the system program may then move on to Gross Analysis 514 and View ECG/Nuclear Data 516 which gives the user an overall view of the data. No user interaction is needed in this section. After the analysis is viewed, the user may chose the regions of data to study in detail.

In Gross analysis, all the data read in is acted on to give a "gross" picture for use in deciding which time periods are of interest for further study. A Beat-to-Beat analysis is performed. Heart rate and ejection fraction are calculated and averaged every 15, 30 or 60 seconds. A graph is then displayed.

Function button inputs from the keyboard 93 are:
1. Background
2. Filtering
3. Start
4. For
5. Average "Background" is used in calculating ejection fraction which may be the measured value or percent of the end diastolic count for each beat. "Filtering" removes some of the statistical fluctuations and the data is easier to view. "Start" is the time to start the analysis, in minutes. "For" is the time period of the analysis, in minutes. "Average" allows the data to be averaged every 15, 30 or 60 seconds. "Running" displays a graph of ejection fraction, heart rate, cardiac output and end diastolic counts.

This is used to view the nuclear data and ECG for periods of time up to 30 seconds. The input buttons from the keyboard 93 are:
1. Filtering
2. Start
3. For "Filtering" permits the nuclear data to be viewed with or without filtering. Filtering removes some of the statistical fluctuations and make the data easier to view. "Start" divides the data into 1 minute groups. Data can only be viewed within a particular 1 minute group. "For" provides the number of seconds to view at a time. The limits are between 1 second and 30 seconds, however, the computer will not let you select a time period that goes beyond the end of a minute.

In Time Range 522, the computer sums the data, smooths the data, and saves it. From the display of raw data, the user indicates a "normal region". The average R-R interval is obtained from this region. The user may input various factors for distinguishing heart beat irregularities. Data is summed by the number of beets or by the time interval as decided by the user. The number of beats or the time interval for summing is also input by the user. A running average of the R-R interval is taken. Beats which are too long or too short are not used in the summation. Each summed beat is smoothed by using an N point quadratic smoothing formula (In a preferred embodiment N=15). The smoothed data for each summation is saved in a file for later display.

Data analysis proceeds along two branches: Summed Beats 518 and Beat-to-Beat 524. The stored smoothed beats are analyzed. The parameters of interest are found and stored in a file. Some of these parameters are:

Average R-R interval & standard deviation, ejection fraction, error in ejection fraction, end dyastolic count, end systolic count, time of end dyastolic count, time of end systolic count, peak ejection, rate and time of occurrence of end systolic count peak ejection, peak fill, and rate and time of occurrence of peak fill.

Data for each beat is smoothed. The ejection fraction is found from the maximum and minimum of each heart beat. The ejection fraction and R-R interval are saved in a file for each heart beat.

As in analysis, presentation branches 530 and 532 according to Summed Beats or Beat-to-Beat. In each case, choices for presentation is made via function buttons on keyboard 93. The meaning of the buttons are different in the two cases and their usage is shown on the bottom line of the display screen 91 of the computer.

In a preferred embodiment, the function buttons available on the keyboard include:
New Parameter
New Time Region
Time Sub region
Previous Time Region
Histogram
Graph
Histogram & Graph
Print Screen
Print Table of values
Exist from presentation For all graphs and histograms produced on the display or on the printer 95, the overall data can be broken up into time periods of interest to the user. Appropriate graphs and histograms may be shown simultaneously.

For both Sum Present (530) and Beat-to-Beat (532), the presentation of a new parameter begins by showing the parameter menu. The following procedure also takes place whenever the New Parameter button is pressed. The parameter is shown as a function of time and as histograms. If the parameter chosen is "waveforms", the summed waveforms are displayed.

Data is presented for a new region of time (always within the main time region). The user is asked to input the starting and stopping times. The portion of the patient schedule within the main time region is shown to help in the time selection. The data for the current parameter, in the current display type (histogram, graph, or both) is shown. The data for a portion of the current time region is expanded. The user can choose the region by manipulating the graphics cursor using arrow keys, or can input starting and stopping time via the keyboard 93. By pressing the Previous Time Region key, the computer goes back to the previously chosen time region. This is useful in choosing another Sub region to expand.

Three types of display can be chosen via the keyboard 93: Histogram(s) of the data, graph(s) of the data as a function of time, and combinations of a graph and a histogram. The display is always of the most current parameter using the current time region.

A copy of the display is presented on the screen 91 of the computer, alone with any needed explanatory messages. A tabular summary of the data on the screen can be printed on printer 95.

Exit from the presentation portion may be accomplished after confirming that the user really wants to leave the presentation portion. The user will be given the following choices. Beat-to-Beat data for the same time period 540, new me period 542, review gross analysis 544, generate final report 546, archive data 548, leave program 550.

For the Beat-to-Beat data the function buttons on the keyboard include:
New Average
Change Parameter
New Time Region
Time Sub-region
Previous Time Region
Histogram
Graph
Histogram & Graph
Print Screen
Print Table of values
Exit from presentation Since there are many more points for some data, Beat-to-Beat data points, in order to fit on the graph, are averaged as needed.

The new average presentation begins with the selection of a new method of averaging. The following procedure also takes place whenever the New Average button is pressed on the keyboard.

The user is asked whether the running average is to be taken over a given number of beats or for a given time period. The user then inputs the number of beats or the time period as selected. A running average of the ejection fraction and R-R interval is performed and the results stored in a file. A graph and a histogram of ejection fraction and R-R interval are shown. The parameters may be changed to ejection fraction, R-R interval, or ejection fraction and R-R interval together. The rest of the buttons are the same as for summed data, except that for Exit, the choice is "Summed Data for same time period" 552.

Auxiliary Data consists of the 4 analog inputs plus the second nuclear data counts. This data can be presented alone with summed data or Beat to Beat data. One or more of these data can be chosen for presentation. In addition, the data can be presented in graphical and/or histogram form without the nuclear cardiac data.

A final report summarizing selected features of the study may be generated. During the Gross Analysis and Gross Presentation portions, the current graphic screen or a table formed from that data may be sent to the printer 95.

Instead of reading in new patient data, the user may begin the session by reading in data previously archived (to floppy and/or magnetic tape). The user will then begin the Gross Analysis, and proceed as normal. At the end of the session, data may be archived to disk or tape. This can be used later to review the patient's data. When beginning a session, if any data is on disk, user is asked if it should be archived, since it has to be erased for a new patient.

Analysis of ECG waves and presentation of the results is similar to results and reports from Holter Monitor type instruments. Correlations are made between ECG and nuclear data.

From the above, it is apparent that many modifications and variations of the present invention are possible in light of the above teachings. For example, it is contemplated that the present ambulatory physiological evaluation system could be used for real-time on-line data analysis where an information transmission cable is connected from the data logger to the computer 92. In this way, information from the main and auxiliary detectors 12 and 14 could be immediately transferred to computer 92 for real time analysis and display. It is also contemplated that the bag 80 which carriers the data logger components could be replaced by a belt that would distribute the weight of the components comfortably about the patient's waist. It is therefore to be understood that, within the scope of the appended claims, the invention may be practiced otherwise than as specifically described.

What is claimed is:

1. An ambulatory evaluation system for monitoring a patient's cardiac activities, said system comprising:
   a vest adapted to be worn about the torso of the patient;
   a main radiation detector for sensing blood volume through the heart of the patient by detection of gamma rays emitted by radiation labeled blood cells;
   a mounting bracket to be mounted to said vest and to receive said main detector;
   first mounting means for adjustably mounting said bracket relative to said vest; and
   second mounting means for adjustably mounting said main detector along two perpendicular directions relative to said bracket.

2. The evaluation system of claim 1 further comprising an auxiliary radiation detector for sensing a predetermined physiological parameter; and
   securing means for securing said auxiliary detector to either said vest or the body of the patient.

3. The evaluation system of claim 2, wherein said securing means comprises a double stick tape with on surface secured to said auxiliary detector and the other surface secured to either said vest or the body of the patient.

4. The evaluation system of claim 1, further comprising storage means for recording and durably storing information relating to the blood volume sensed by said main radiation detector over a desired period of time.

5. The evaluation system of claim 4, further comprising:

retrieving means for retrieving said stored information; and
display means for presenting said retrieved information in readable format.

6. The evaluation system of claim 4, wherein said storage means includes means for carrying by the patient and said retrieving means and said display means include a stand alone device.

* * * * *